(12) United States Patent
Yang et al.

(10) Patent No.: US 9,127,305 B2
(45) Date of Patent: Sep. 8, 2015

(54) METHODS FOR PERFORMING DIRECT ENZYMATIC REACTIONS INVOLVING NUCLEIC ACID MOLECULES

(75) Inventors: Young Geun Yang, Seoul (KR); Jong Yeol Kim, Seoul (KR); Suhng Wook Kim, Gyeonggi-do (KR); Sung Gwan Lee, Seoul (KR)

(73) Assignee: BIOQUEST, INC., Seoul (KR)

( * ) Notice: Subject to any disclaimer, the term of this patent is extended or adjusted under 35 U.S.C. 154(b) by 881 days.

(21) Appl. No.: 11/817,151

(22) PCT Filed: Feb. 8, 2006

(86) PCT No.: PCT/KR2006/000457
§ 371 (c)(1),
(2), (4) Date: Dec. 21, 2007

(87) PCT Pub. No.: WO2006/090987
PCT Pub. Date: Aug. 31, 2006

(65) Prior Publication Data
US 2009/0155777 A1 Jun. 18, 2009

(30) Foreign Application Priority Data
Feb. 28, 2005 (KR) .......................... 10-2005-0016481

(51) Int. Cl.
| C12Q 1/68 | (2006.01) |
| C12P 19/34 | (2006.01) |
| C07H 21/04 | (2006.01) |
| G01N 31/22 | (2006.01) |
| G01N 33/52 | (2006.01) |

(52) U.S. Cl.
CPC ............ C12Q 1/6806 (2013.01); C12Q 1/6827 (2013.01); C12Q 1/6844 (2013.01)

(58) Field of Classification Search
USPC .......... 435/6.1, 6.12, 91.2; 536/24.3; 422/430
See application file for complete search history.

(56) References Cited

U.S. PATENT DOCUMENTS

| 4,437,975 A | 3/1984 | Gillespie et al. |
| 4,683,195 A | 7/1987 | Mullis et al. |
| 4,683,202 A | 7/1987 | Mullis |
| 4,800,159 A | 1/1989 | Mullis et al. |
| 4,988,617 A | 1/1991 | Landegren et al. |
| 5,130,238 A | 7/1992 | Malek et al. |
| 5,242,794 A | 9/1993 | Whiteley et al. |
| 5,413,909 A | 5/1995 | Bassam et al. |
| 5,501,963 A * | 3/1996 | Burckhardt .................. 435/91.2 |
| 5,545,525 A | 8/1996 | Montplaisir et al. |
| 5,554,517 A | 9/1996 | Davey et al. |
| 5,702,944 A * | 12/1997 | Racioppi et al. .......... 435/253.6 |
| 5,846,717 A | 12/1998 | Brow et al. |
| 5,935,825 A | 8/1999 | Nishimura et al. |
| 5,994,069 A | 11/1999 | Hall et al. |
| 6,001,567 A | 12/1999 | Brow et al. |
| 6,063,603 A | 5/2000 | Davey et al. |
| 6,090,543 A | 7/2000 | Prudent et al. |
| 6,410,276 B1 | 6/2002 | Burg et al. |
| 6,413,747 B1 | 7/2002 | Kato et al. |
| 6,576,447 B2 * | 6/2003 | Tonoike ....................... 435/91.1 |
| 6,582,938 B1 | 6/2003 | Su et al. |
| 6,667,165 B2 | 12/2003 | Peters |
| 7,575,864 B2 * | 8/2009 | Bedzyk et al. ............... 435/6.12 |
| 7,727,718 B2 * | 6/2010 | Chomczynski .................... 435/6 |
| 2004/0259106 A1 * | 12/2004 | Gunderson et al. ............... 435/6 |
| 2005/0260606 A1 * | 11/2005 | Kermekchiev et al. ........... 435/6 |
| 2006/0115844 A1 * | 6/2006 | Finkelstein et al. ............... 435/6 |
| 2007/0117094 A1 * | 5/2007 | Hayashizaki et al. ............ 435/6 |

FOREIGN PATENT DOCUMENTS

| EP | 329822 B1 | 6/1994 |
| EP | 439182 B1 | 4/1996 |
| KR | 10-0746372 B1 | 8/2007 |
| WO | 88/10315 A1 | 12/1988 |
| WO | 89/06700 A1 | 7/1989 |
| WO | 90/01069 A1 | 2/1990 |
| WO | 90/06995 A1 | 6/1990 |
| WO | 9314225 A1 | 7/1993 |
| WO | 03/006650 A1 | 1/2003 |

OTHER PUBLICATIONS

Ledford et al, A muli-site study for detection of the factor V (leiden) mutation from genomic DNA using a homogeneous Invader microtiter plate FRET assay, 2000, Journal of Molecular Diagnostics, 2, 97-104.*
Invitrogen Platinum Taq DNA polymerase Brochure, down loaded from the internet [ www.invitrogen.com], printed Aug. 26, 2012, pp. 1-4.*
Fode-Vaughan et al, Detection of Bacteria in Environmental Samples by Direct PCR Without DNA Extraction, 2001, Biotechniques, 31, 598-607.*
Nishimura et al, Direct polymerase chain reaction from whole blood without DNA isolation, 2000, Am. Clin. Biochem, 37, 674-680.*
Raskin et al, Cystic fibrosis genotyping by direct PCR analysis of Guthrie blood spots, 1992, Genome Res., 2,154-156.*
Spiess et al, Trehalose Is a Potent PCR Enhancer: Lowering of DNA Melting Temperature and Thermal Stabilization of Taq Polymerase by the Disaccharide Trehalose, 2004, Clinical Chemistry, 50, 1256-1259.*
Tamanai-Shacoori et al., "Comparison of direct PCR and PCR amplification after DNA extraction—for the detection of viable enterotoxigenic *Escherichia coli* in laboratory microcosms", Journal of Microbiological Methods 26 (1996) 21-26.

* cited by examiner

*Primary Examiner* — Narayan Bhat
(74) *Attorney, Agent, or Firm* — The PL Law Group, PLLC

(57) ABSTRACT

Methods for performing a direct enzymatic reaction involving a nucleic acid molecule include performing the enzymatic reaction directly using a biological specimen in a reaction mixture containing a zwitterionic buffer and/or a non-reducing carbohydrate to prevent the biological specimen from inhibiting the enzymatic reaction, in which a nucleic acid molecule present in the biological specimen is not purified before the enzymatic reaction, and obtaining a product from the enzymatic reaction.

12 Claims, 16 Drawing Sheets

SEQUENCE LISTING

```
<160> NUMBER OF SEQ ID NOS: 36

<210> SEQ ID NO 1
<211> LENGTH: 20
<212> TYPE: DNA
<213> ORGANISM: Artificial Sequence
<220> FEATURE:
<223> OTHER INFORMATION: GH20 sense primer

<400> SEQUENCE: 1
caacttcatc cacgttcacc                                                   20

<210> SEQ ID NO 2
<211> LENGTH: 21
<212> TYPE: DNA
<213> ORGANISM: Artificial Sequence
<220> FEATURE:
<223> OTHER INFORMATION: GH21 antisense primer

<400> SEQUENCE: 2
ggaaaataga ccaataggca g                                                 21

<210> SEQ ID NO 3
<211> LENGTH: 22
<212> TYPE: DNA
<213> ORGANISM: Artificial Sequence
<220> FEATURE:
<223> OTHER INFORMATION: KM38 primer
```

```
<400> SEQUENCE: 3
tggtctcctt aaacctgtct tg                                      22

<210> SEQ ID NO 4
<211> LENGTH: 20
<212> TYPE: DNA
<213> ORGANISM: Artificial Sequence
<220> FEATURE:
<223> OTHER INFORMATION: E6f primer

<400> SEQUENCE: 4
tgttcacttg tgccctgact                                         20

<210> SEQ ID NO 5
<211> LENGTH: 19
<212> TYPE: DNA
<213> ORGANISM: Artificial Sequence
<220> FEATURE:
<223> OTHER INFORMATION: E6r primer

<400> SEQUENCE: 5
ggagggccac tgacaacca                                          19

<210> SEQ ID NO 6
<211> LENGTH: 18
<212> TYPE: DNA
<213> ORGANISM: Artificial Sequence
<220> FEATURE:
<223> OTHER INFORMATION: E1SD primer

<400> SEQUENCE: 6
caggacagcg gcccggag                                           18

<210> SEQ ID NO 7
<211> LENGTH: 18
<212> TYPE: DNA
<213> ORGANISM: Artificial Sequence
<220> FEATURE:
<223> OTHER INFORMATION: I1SD primer

<400> SEQUENCE: 7
ctgcagacgc tccgccgt                                           18

<210> SEQ ID NO 8
<211> LENGTH: 18
<212> TYPE: DNA
<213> ORGANISM: Artificial Sequence
<220> FEATURE:
<223> OTHER INFORMATION: apoE-f primer

<400> SEQUENCE: 8
ggcacggctg tccaagga                                           18

<210> SEQ ID NO 9
<211> LENGTH: 18
<212> TYPE: DNA
<213> ORGANISM: Artificial Sequence
<220> FEATURE:
<223> OTHER INFORMATION: apoE-r primer

<400> SEQUENCE: 9
ctcgcggatg gcgctgag                                           18

<210> SEQ ID NO 10
<211> LENGTH: 30
```

```
<212> TYPE: DNA
<213> ORGANISM: Artificial Sequence
<220> FEATURE:
<223> OTHER INFORMATION: SK145 primer

<400> SEQUENCE: 10
agtgggggga catcaagcag ccatgcaaat                                          30

<210> SEQ ID NO 11
<211> LENGTH: 27
<212> TYPE: DNA
<213> ORGANISM: Artificial Sequence
<220> FEATURE:
<223> OTHER INFORMATION: SK431 primer

<400> SEQUENCE: 11
tgctatgtca gttccccttg gttctct                                             27

<210> SEQ ID NO 12
<211> LENGTH: 28
<212> TYPE: DNA
<213> ORGANISM: Artificial Sequence
<220> FEATURE:
<223> OTHER INFORMATION: SK38 primer

<400> SEQUENCE: 12
ataatccacc tatcccagta ggagaaat                                            28

<210> SEQ ID NO 13
<211> LENGTH: 28
<212> TYPE: DNA
<213> ORGANISM: Artificial Sequence
<220> FEATURE:
<223> OTHER INFORMATION: SK39 primer

<400> SEQUENCE: 13
tttggtcctt gtcttatgtc cagaatgc                                            28

<210> SEQ ID NO 14
<211> LENGTH: 24
<212> TYPE: DNA
<213> ORGANISM: Artificial Sequence
<220> FEATURE:
<223> OTHER INFORMATION: E8f primer

<400> SEQUENCE: 14
gacaagggtg gttgggagta gatg                                                24

<210> SEQ ID NO 15
<211> LENGTH: 20
<212> TYPE: DNA
<213> ORGANISM: Artificial Sequence
<220> FEATURE:
<223> OTHER INFORMATION: E-R2 primer

<400> SEQUENCE: 15
cacaaacacg cacctcaaag                                                     20

<210> SEQ ID NO 16
<211> LENGTH: 21
<212> TYPE: DNA
<213> ORGANISM: Artificial Sequence
<220> FEATURE:
<223> OTHER INFORMATION: b-actin-f primer

<400> SEQUENCE: 16
```

```
caagagatgg ccacggctgc t                                       21

<210> SEQ ID NO 17
<211> LENGTH: 21
<212> TYPE: DNA
<213> ORGANISM: Artificial Sequence
<220> FEATURE:
<223> OTHER INFORMATION: b-actin-r primer

<400> SEQUENCE: 17
tccttctgca tcctgtcggc a                                       21

<210> SEQ ID NO 18
<211> LENGTH: 20
<212> TYPE: DNA
<213> ORGANISM: Artificial Sequence
<220> FEATURE:
<223> OTHER INFORMATION: MC1R-f primer

<400> SEQUENCE: 18
caagaaccgc aacctgcact                                         20

<210> SEQ ID NO 19
<211> LENGTH: 20
<212> TYPE: DNA
<213> ORGANISM: Artificial Sequence
<220> FEATURE:
<223> OTHER INFORMATION: MC1R-r primer

<400> SEQUENCE: 19
tgatgaagag caggctggtg                                         20

<210> SEQ ID NO 20
<211> LENGTH: 26
<212> TYPE: DNA
<213> ORGANISM: Artificial Sequence
<220> FEATURE:
<223> OTHER INFORMATION: vir-f primer

<400> SEQUENCE: 20
ctgcattctg gcaatctctt cacatc                                  26

<210> SEQ ID NO 21
<211> LENGTH: 26
<212> TYPE: DNA
<213> ORGANISM: Artificial Sequence
<220> FEATURE:
<223> OTHER INFORMATION: vir-r primer

<400> SEQUENCE: 21
tgatgagcta acttcgtaag ccctcc                                  26

<210> SEQ ID NO 22
<211> LENGTH: 20
<212> TYPE: DNA
<213> ORGANISM: Artificial Sequence
<220> FEATURE:
<223> OTHER INFORMATION: sense primer

<400> SEQUENCE: 22
tccatcttgg catctctcag                                         20

<210> SEQ ID NO 23
<211> LENGTH: 20
<212> TYPE: DNA
<213> ORGANISM: Artificial Sequence
```

```
<220> FEATURE:
<223> OTHER INFORMATION: antisense primer

<400> SEQUENCE: 23
gtacccgcat caggcatctg                                          20

<210> SEQ ID NO 24
<211> LENGTH: 26
<212> TYPE: DNA
<213> ORGANISM: Artificial Sequence
<220> FEATURE:
<223> OTHER INFORMATION: E18F1 primer

<400> SEQUENCE: 24
aatgagctgg caagtgccgt gtcctg                                   26

<210> SEQ ID NO 25
<211> LENGTH: 27
<212> TYPE: DNA
<213> ORGANISM: Artificial Sequence
<220> FEATURE:
<223> OTHER INFORMATION: E18R1 primer

<400> SEQUENCE: 25
cctctcaata acttgggaaa aacactg                                  27

<210> SEQ ID NO 26
<211> LENGTH: 27
<212> TYPE: DNA
<213> ORGANISM: Artificial Sequence
<220> FEATURE:
<223> OTHER INFORMATION: E19F1 primer

<400> SEQUENCE: 26
agcccccagc aatatcagcc ttaggtg                                  27

<210> SEQ ID NO 27
<211> LENGTH: 27
<212> TYPE: DNA
<213> ORGANISM: Artificial Sequence
<220> FEATURE:
<223> OTHER INFORMATION: E19R1 primer

<400> SEQUENCE: 27
atgggagagg ccagtgctgt ctctaag                                  27

<210> SEQ ID NO 28
<211> LENGTH: 26
<212> TYPE: DNA
<213> ORGANISM: Artificial Sequence
<220> FEATURE:
<223> OTHER INFORMATION: E20F1 primer

<400> SEQUENCE: 28
gcattcatgc gtcttcacct ggaagg                                   26

<210> SEQ ID NO 29
<211> LENGTH: 27
<212> TYPE: DNA
```

```
<213> ORGANISM: Artificial Sequence
<220> FEATURE:
<223> OTHER INFORMATION: E20R1 primer

<400> SEQUENCE: 29
gcacacacat atccccatgg caaactc                                              27

<210> SEQ ID NO 30
<211> LENGTH: 27
<212> TYPE: DNA
<213> ORGANISM: Artificial Sequence
<220> FEATURE:
<223> OTHER INFORMATION: E21F1 primer

<400> SEQUENCE: 30
cgccagccat aagtcctcga cgtggag                                              27

<210> SEQ ID NO 31
<211> LENGTH: 27
<212> TYPE: DNA
<213> ORGANISM: Artificial Sequence
<220> FEATURE:
<223> OTHER INFORMATION: E21R1 primer

<400> SEQUENCE: 31
tctggagagc atcctcccct gcatgtg                                              27

<210> SEQ ID NO 32
<211> LENGTH: 20
<212> TYPE: DNA
<213> ORGANISM: Artificial Sequence
<220> FEATURE:
<223> OTHER INFORMATION: egfr-f primer

<400> SEQUENCE: 32
ggcccgcgcg agctagacgt                                                      20

<210> SEQ ID NO 33
<211> LENGTH: 22
<212> TYPE: DNA
<213> ORGANISM: Artificial Sequence
<220> FEATURE:
<223> OTHER INFORMATION: egfr-r primer

<400> SEQUENCE: 33
caggtggcct gtcgtccggt ct                                                   22

<210> SEQ ID NO 34
<211> LENGTH: 20
<212> TYPE: DNA
<213> ORGANISM: Artificial Sequence
<220> FEATURE:
<223> OTHER INFORMATION: egfr-sbe primer

<400> SEQUENCE: 34
gcgcggccgc agcagcctcc                                                      20

<210> SEQ ID NO 35
<211> LENGTH: 21
<212> TYPE: DNA
<213> ORGANISM: Artificial Sequence
<220> FEATURE:
<223> OTHER INFORMATION: L15996 primer

<400> SEQUENCE: 35
ctccaccatt agcacccaaa g                                                    21
```

```
<210> SEQ ID NO 36
<211> LENGTH: 20
<212> TYPE: DNA
<213> ORGANISM: Artificial Sequence
<220> FEATURE:
<223> OTHER INFORMATION: H16401 primer

<400> SEQUENCE: 36
tgatttcacg gaggatggtg                                          20
```

METHODS FOR PERFORMING DIRECT ENZYMATIC REACTIONS INVOLVING NUCLEIC ACID MOLECULES

CROSS-REFERENCES TO RELATED APPLICATIONS

This is a US National Stage under 35 USC §371 of International application PCT/KR2006/000457, which was filed with the Republic of Korea Receiving Office on Feb. 8, 2006, and which is incorporated herein by reference. The benefit of priority is further claimed to Republic of Korea application 10-2005-0016481, which was filed with the Korean Intellectual Property Office on Feb. 28, 2005, and which is also incorporated herein by reference.

The Sequence Listing submitted in text format (.txt) on Jul. 30, 2010, named "11_817151_Sequence_Listing.txt, (created on Friday, Jul. 30, 2010, 8 KB), is incorporated herein by reference.

FIELD OF THE INVENTION

The present invention relates to methods for performing a direct enzymatic reaction involving a nucleic acid molecule and directly using a biological specimen, and kits therefor.

BACKGROUND

Nucleic acid molecules have become the most important subject and object in molecular biology since the double helix structure of DNA was elucidated by Watson and Crick. In addition, enzymes using nucleic acid molecules as substrates or templates have been extensively developed and studied, and various technologies to manipulate nucleic acid molecules have been suggested, including cloning and mutagenesis.

Mullis et al. (1-3) have developed a polymerase chain reaction (PCR) in the end of 1980s to take a giant step in molecular biology. Besides, a wide variety of nucleic acid-manipulating technologies such as ligase chain reaction (LCR), branched DNA technology (bDNA), transcription mediated amplification (TMA), hybridization protection assay (HPA), hybrid capture system, strand displacement amplification (SDA), cycling probe technology (CPT), real-time PCR, Invader assay and loop-mediated isothermal amplification (LAMP) have been reported to meet a number of requirements in the research and industry fields such as genetic engineering, protein engineering, diagnostics and therapeutics.

As such, nucleic acid molecules are widely used in various fields; and their applications are accompanied indispensably with pre-purification (isolation) processes. In other words, since biological specimens containing nucleic acid molecules are very likely to contain inhibitors against enzymatic reactions, inter alia, enzymes, the nucleic acid molecules are required to be isolated from the inhibitors before application. For example, a PCR process generally uses a nucleic acid molecule as templates purified from biological specimens, because various substances present in biological specimens inhibit a PCR process, thereby not giving desired results.

To isolate or purify nucleic acid molecules from biological specimens, phenol-chloroform extraction, ion-exchange chromatography or glass bead-using method are usually employed. However, these purification methods considered to be tedious are a time- and cost-consuming process. Furthermore, phenol is well known to be very toxic to human and environment. Accordingly, if biological specimens can be applied directly to nucleic acid-involving enzymatic reactions, many advantages are induced.

Blood samples are subjects to be analyzed with the amplification reactions, in particular, PCR. However, blood samples have inherent limitations in applying directly to the amplification reactions, because various enzyme inhibitors to polymerase are present in blood samples. The inherent inhibitors include heme (4), immunoglobulin G (Ig G) (5), salts (e.g., $K^+$ and $Na^+$), bile salts, and DNase and proteinases in blood cells. In addition, anticoagulants such as EDTA, heparin and sodium citrate show the strong inhibition activity against amplification reactions, inter alia, PCR.

Where the direct amplification reaction without nucleic acid purification is practical, many drawbacks associated with nucleic acid purification can be overcome, including (i) infection of researchers; (ii) cross-contamination between nucleic acid samples; (iii) loss of nucleic acid, particularly when a trace amount of sample is present; (iv) loss of time and cost; and (v) difficulty in automation. In this regard, many researches have suggested methods for performing direct enzymatic reactions.

For instance, Mercier et al. (6), Panaccio et al. (7) and McCusker et al. (8) have reported the PCR processes directly using blood samples. In addition, Panaccio et al. (9) have also suggested the direct PCR process using blood samples. However, this process has some shortcomings in that blood samples are mixed with formamide and the mixture undergoes pre-reaction (9, 10). Burckhardt discloses that varying the concentration of cations in PCR reactions allows for the direct PCR using up to 80% (v/v) blood sample(11). According to Burckhardt's suggestion, the formulation and composition of PCR reactions are varied depending on the amount of blood samples and blood samples are pre-heated prior to amplification reactions.

Even though the reports described previously describe the possibility to conduct the direct PCR using blood samples, inconveniences such as requirements to a single-stranded DNA-binding protein (T4 gene 32 protein (gp32)) (12) or specific pretreatments remain to be solved (8, 13).

Recently, some researchers including Makowski et al. (14), Kreader(12), and Satoh et al.(15) have also reported direct PCR reactions.

Al-Soud et al. have studied DNA samples, isolated from bacteria, which were mixed with different amounts of biological specimens such as blood, feces, and suspensions of cheese and meat and then PCR-amplified using various thermostable DNA polymerases and PCR facilitators(16). As a result, they have found that bovine serum albumin (BSA), betaine and gp32 could prevent blood samples from inhibiting PCR reactions. However, their tests used DNA samples artificially mixed with biological specimens such as blood rather than biological specimens per se, not reflecting a real realm of direct amplification reactions. Furthermore, they employed a relatively high content of DNA samples (1 ng/25 μl reaction), so that they did not evaluate whether the trace amount of DNA samples could be amplified using such PCR facilitators.

Nishimura et al. have proposed that PCR reactions at pH range higher than 8.9 could considerably overcome the inhibition effect of blood to PCR (U.S. Pat. No. 5,935,825). In addition, they have suggested a high level of polyamines enabled the direct PCR reactions using feces to be possible (U.S. Pat. No. 6,413,747). However, since their approaches adopt higher pH, chemically modified DNA polymerases hot start PCR such as AmpliTaq Gold DNA polymerase (Applied Biosystems, Inc.), FastStart Taq DNA polymerase (Roche Applied Science, Inc.) and HotStarTaq DNA polymerase (Qiagen, Inc.) do not work under their conditions, and various DNA polymerases are not applied to their PCR reactions.

In addition, Kato et al. have suggested direct amplification reactions of low copy DNA molecules using polyamines (U.S. Pat. No. 6,413,747). However, they have not employed blood samples directly. Instead, they have used indirectly collected leukocyte samples having added human immunodeficiency virus type 1 (HIV-1) DNA molecules, which was free from PCR inhibitors such as heme. Therefore, it is unreasonable that their results are given by preventing blood samples from inhibiting PCR activity.

Accordingly, there remains a long-felt need in the art to develop a novel direct enzymatic reaction (particularly, amplification reaction) without nucleic acid purification.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY

Under such circumstances, the present inventors have performed intensive research to develop a novel approach for conducting a direct enzymatic reaction involving nucleic acid molecules directly using biological specimens, and as a result, discovered that a zwitterionic buffer and/or a non-reducing carbohydrate contained in a reaction mixture enables the direct enzymatic reaction to be practical without pre-purification of nucleic acid molecules contained in biological specimens.

Accordingly, it is an object to provide a method for performing a direct enzymatic reaction involving a nucleic acid molecule and directly using a biological specimen.

It is another object to provide a kit for performing a direct enzymatic reaction involving a nucleic acid molecule and directly using a biological specimen.

It is still another object to provide a method for preventing a biological specimen from inhibiting an enzymatic reaction involving a nucleic acid molecule.

It is further object to provide a use of a zwitterionic buffer and/or a non-reducing carbohydrate for manufacturing a reaction mixture for a direct enzymatic reaction involving a nucleic acid molecule.

In one aspect, there is provided a method for performing a direct enzymatic reaction involving a nucleic acid molecule, which includes performing the enzymatic reaction directly using a biological specimen in a reaction mixture containing a zwitterionic buffer and/or a non-reducing carbohydrate to prevent the biological specimen from inhibiting the enzymatic reaction, in which a nucleic acid molecule present in the biological specimen is not purified before the enzymatic reaction, and obtaining a product from the enzymatic reaction.

In another aspect, there is provided a kit for performing a direct enzymatic reaction involving a nucleic acid molecule and directly using a biological specimen, which includes a reaction mixture for the enzymatic reaction containing a zwitterionic buffer and/or a non-reducing carbohydrate to prevent the biological specimen from inhibiting the enzymatic reaction, in which the nucleic acid molecule present in the biological specimen is not required to be purified before the enzymatic reaction.

Other objects and advantages of the present invention will become apparent from the detailed description to follow and in view of the appended claims and drawings.

DETAILED DESCRIPTION

Figure 1:
FIG. 1 shows the direct PCR (polymerase chain reaction) results of the β-globin gene (408 bp) using a primer set GH20/GH21. Lanes 1-9 correspond to Tris-buffer (pH 8.3, 8.4, 8.5, 8.6, 8.7, 8.8, 8.9, 9.0 and 9.2, respectively), lanes 10-20 to Tricine-buffer (pH 8.0, 8.1, 8.2, 8.3, 8.4, 8.5, 8.6, 8.7, 8.8, 8.9 and 9.0, respectively), lanes 21-29 to Bicine-buffer (pH 8.0, 8.1, 8.2, 8.3, 8.4, 8.5, 8.6, 8.7 and 8.8, respectively), and lanes 30-40 to HEPES-buffer (pH 8.0, 8.1, 8.2, 8.3, 8.4, 8.5, 8.6, 8.7, 8.8, 8.9 and 9.0, respectively). L denotes a 100 bp ladder ranging from 100 to 1500 bp.

The present inventors have performed intensive research to develop a novel approach for conducting a direct enzymatic reaction involving nucleic acid molecules directly using biological specimens, and as a result, discovered that a zwitterionic buffer and/or a non-reducing carbohydrate contained in a reaction mixture enables the direct enzymatic reaction to be practical without pre-purification of nucleic acid molecules contained biological specimens.

The success in the direct enzymatic reaction using biological specimens relies on how to prevent biological specimens from inhibiting enzymatic reactions. The term "direct enzymatic reaction" used herein refers to a reaction catalyzed by enzymes directly using biological specimens without any pretreatment for isolating or purifying certain biological substance contained in biological specimens.

Biological specimens such as body fluid (e.g., blood, saliva and lymph) and cell culture carry generally inherent inhibitors to enzymatic reactions, inter alia, enzymes per se. The present invention completely ensures to overcome limitations associated with enzyme inhibitors present in biological specimens, thereby permitting a successful direct enzymatic reaction using biological specimens with higher efficiency and applicability.

The term "enzymatic reaction involving nucleic acid molecules" used herein refers to a reaction catalyzed by an enzyme employing nucleic acid molecules as substrates, templates or primers. The enzymatic reaction involving nucleic acid molecules gives rise to the modification of nucleic acid molecules. The term "nucleic acid" used herein refers to a deoxyribonucleotide or ribonucleotide polymer in either single or double-stranded form.

The present invention allows for the direct enzymatic reaction using biological specimens with higher efficiency and applicability, not requiring any pretreatment to isolate or purify nucleic acid molecules present in biological specimens.

The present invention can be applied to a wide variety of nucleic acid (NA)-involved enzymatic reactions. Preferably, the present invention is applied to an amplification reaction, a reverse transcription, a DNA ligation, a nuclease-mediated reaction, DNA methylation, topoisomerase-mediated reaction or telomerase-mediated reaction.

The term "amplification reaction" is used to refer to a reaction for amplifying a nucleic acid molecule. A multitude of amplification reactions have been suggested in the art, including polymerase chain reaction (hereinafter referred to as PCR) (U.S. Pat. Nos. 4,683,195, 4,683,202, and 4,800,159), reverse transcription-polymerase chain reaction (hereinafter referred to as RT-PCR) (Sambrook, J. et al., *Molecular Cloning. A Laboratory Manual*, 3rd ed. Cold Spring Harbor Press (2001)), the methods of Miller, H. I. (WO 89/06700) and Davey, C. et al. (EP 329,822), ligase chain reaction (LCR) (17, 18), Gap-LCR (WO 90/01069), repair chain reaction (EP 439,182), transcription-mediated amplification (TMA) (19) (WO 88/10315), self sustained sequence replication(20) (WO 90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909 and 5,861,245), nucleic acid sequence based amplification (NASBA) (U.S. Pat. Nos. 5,130,238, 5,409,818, 5,554,517, and 6,063,603), strand displacement amplification(21, 22) and loop-mediated isothermal amplification (LAMP)(23), but not limited to. Other amplification methods that may be used are described in, U.S. Pat. Nos. 5,242,794, 5,494,810, 4,988,617 and in U.S. Ser. No. 09/854,317.

The term "reverse transcription" is used herein to mean a reaction to synthesize DNA on an RNA template. For example, the reverse transcription is involved in RT-PCR. The term "DNA ligation" is intended to refer to a reaction to form a covalent linkage between two DNA molecules. For instance, the DNA ligation is involved in LCR.

The term "nuclease-mediated reaction" as used herein means a reaction catalyzed by nucleases to cleave phosphodiester bonds in a nucleic acid molecule. There are a number of nucleases known to one skilled in the art. For example, nucleases include, but not limited to, endonucleases (e.g., FEN-1 endonuclease, restriction enzyme, DNase I, DNase II and RNase I) and exonucleases (snake venom phosphodiesterase and spleen phosphodiesterase). For example, FEN-1 endonuclease plays a pivotal role in Invader assay.

A "DNA methylation", as the term is used herein, means a reaction to cause methylation at certain position of bases on DNA. A "topoisomerase-mediated reaction", as the term is used herein, refers to a reaction catalyzed by topoisomerases (e.g., type I or II topoisomerase) to convert one topological isomer of covalently closed circle DNA to another. The term "telomerase-mediated reaction" refers to a reaction catalyzed by telomerase to cause the generation of repeating units of one strand at the telomere.

According to a preferred embodiment, the enzymatic reaction is the amplification reaction. Where the present method is carried out for amplifying a target nucleic acid molecule, it may be conducted using a reaction mixture containing the zwitterionic buffer and/or the non-reducing carbohydrate in accordance with procedures as described in references identified hereinabove. Preferably, the direct amplification of this invention comprises the steps of (i) obtaining a biological specimen containing a target nucleic acid molecule; (ii) contacting the biological specimen to a reaction mixture for the amplification reaction containing an enzyme plus the zwitterionic buffer and/or the non-reducing carbohydrate to prevent the biological specimen from inhibiting the amplification reaction; and (iii) amplifying the target nucleic acid molecule.

The term "direct amplification" used herein refers to an amplification reaction using directly biological specimens without any pretreatment for isolating or purifying nucleic acid molecules contained in biological specimens.

The enzyme contained in the reaction mixture includes, but not limited to, a thermostable DNA polymerase for PCR-based amplification, a thermostable ligase for LCR, and reverse transcriptase, RNase H and RNA polymerase for NASBA and TMA.

According to a more preferred embodiment, the enzymatic reaction is PCR-based amplifications.

PCR is one of the most predominant processes for nucleic acid amplification and a number of its variations and applications have been developed. For example, for improving PCR specificity or sensitivity, touchdown PCR(24), hot start PCR(25, 26), nested PCR(2) and booster PCR(27) have been developed with modifying traditional PCR procedures. In addition, real-time PCR, differential display PCR (DD-PCR), rapid amplification of cDNA ends (RACE), multiplex PCR, inverse polymerase chain reaction (IPCR), vectorette PCR, thermal asymmetric interlaced PCR (TAIL-PCR) and multiplex PCR have been suggested for certain applications. The details of PCR can be found in McPherson, M. J., and Moller, S. G. *PCR*. BIOS Scientific Publishers, Springer-Verlag New York Berlin Heidelberg, N.Y. (2000), the teachings of which are incorporated herein by reference in its entity.

While a multitude of PCR-based amplification methods have been reported, they follow common steps such as thermal cycling and use of thermostable DNA polymerase.

Where the present invention is performed in accordance with PCR-based amplifications, it may comprise the steps of (i) obtaining a biological specimen containing a target nucleic acid molecule; (ii) contacting the biological specimen to a reaction mixture for PCR containing a thermostable DNA polymerase plus the zwitterionic buffer and/or the non-reducing carbohydrate to prevent the biological specimen from inhibiting the amplification reaction; and (iii) amplifying the target nucleic acid molecule.

The thermostable DNA polymerase contained the PCR reaction may be one isolated from thermophilic Eubacteria or Archaebacteria, for example, *Thermus aquaticus, T. thermophilus, T. bockianus, T. flavus, T. rubber, Thermococcus litoralis, Pyrococcus furiousus, P. wosie, Pyrococcus* spec. KGD, *Thermatoga maritime, Thermoplasma acidophilus,* and *Sulfolobus* spec. Preferably, the thermostable DNA polymerase is Taq DNA polymerase, Tth DNA polymerase, Pfu DNA polymerase, Pwo DNA polymerase and modified thermostable DNA polymerase for the inactivation at room temperature.

The modified thermostable DNA polymerase for the inactivation at room temperature includes chemically modified thermostable DNA polymerase and antibody-bound thermostable DNA polymerase. The term "chemically modified (or chemical-modified) thermostable DNA polymerase" used herein means a thermostable DNA polymerase chemically modified for the inactivation at room temperature, which has been developed for hot start PCR. The chemically modified thermostable DNA polymerase is regenerated in initial regeneration step (e.g., heating for 10 min at 95° C.) and then undertakes PCR. Non-limiting examples of the chemically modified thermostable DNA polymerase commercially available include AmpliTaq Gold DNA polymerase (Applied Biosystem, Inc.), FastStart Taq DNA polymerase (Roche Applied Science, Inc.) and HotStarTaq DNA polymerase (Qiagen, Inc.). The antibody-bound thermostable DNA polymerase is inactive at room temperature due to the bound antibody and becomes active upon the denaturation of antibody at high temperature.

When the amplification reaction, is being conducted, it is preferable to provide the components required for such reaction in excess in the reaction vessel. Excess in reference to components of the amplification reaction refers to an amount of each component such that the ability to achieve the desired amplification is not substantially limited by the concentration of that component. It is desirable to provide to the reaction mixture an amount of required cofactors such as $Mg^{2+}$, and dATP, dCTP, dGTP and dTTP in sufficient quantity to support the degree of amplification desired.

The conditions for the amplification are well known to those of skill in the art and described in various publications such as Joseph Sambrook, et al., *Molecular Cloning, A Laboratory Manual*, Cold Spring Harbor Laboratory Press, Cold Spring Harbor, N.Y. (2001) and McPherson, M. J., and Moller, S. G. *PCR*. BIOS Scientific Publishers, Springer-Verlag New York Berlin Heidelberg, N.Y. (2000), teachings of which are incorporated herein by reference in their entity. The direct PCR of this invention may be carried out in accordance with general procedures and conditions for PCR known to one skilled in the art, except that a biological specimen is directly used instead of isolated nucleic acid template and a zwitterionic buffer and/or a non-reducing carbohydrate are used in the reaction mixture.

According to a preferred embodiment, the present invention is performed in accordance with RT-PCR. Surprisingly, the present invention enables the direct RT-PCR without RNA isolation to be practicable. The direct RT-PCR of this invention comprises the step of reverse transcription for producing cDNA from mRNA prior to amplification step, details of which are found in Joseph Sambrook, et al., *Molecular Cloning, A Laboratory Manual*, Cold Spring Harbor Laboratory Press, Cold Spring Harbor, N.Y. (2001); and Noonan, K. F. et al.(28). For reverse transcription, an oligonucleotide dT primer hybridizable to poly A tail of mRNA is used. Reverse transcription can be done with a reverse transcriptase, e.g., reverse transcriptase derived from MMLV (Moloney Murine Leukemia Virus), AMV (Avian Myeloblastosis Virus) or HIV (Human Immunodeficiency Virus).

According to a preferred embodiment, the present invention is applied to hot start PCR. Host start PCR has been developed to increase PCR sensitivity and specificity(25). Amplification reactions for infectious diseases or forensic science usually use nucleic acid samples with low copy number. In particular, for diagnosis of infectious diseases such as HIV- and HBV-associated diseases, earlier detection of viral infection is very important. In other words, viral nucleic acid molecules present in low copy number have to be amplified for giving accurate and reliable diagnosis results. According to the present invention, nucleic acid molecules in low copy number can be amplified by hot start PCR directly using biological specimens. Such achievement in this invention is ascribed to the use of a zwitterionic buffer and/or a non-reducing carbohydrate to prevent the biological specimen from inhibiting an enzymatic reaction. Such action of a zwitterionic buffer and/or a non-reducing carbohydrate can exert at relatively lower pH (e.g., pH 8.3) than that (e.g., pH 9.0) previously reported (U.S. Pat. No. 5,9325,825), so that hot start PCR with chemically modified polymerases may be successfully performed using biological specimens under conditions provided by the present invention.

In addition, the present invention can be applied to other hot start PCR variations using polymerase inhibitors at room temperature such as dextran sulfate (U.S. Pat. No. 6,667,165) or aptamer(29, 30).

General procedures and conditions for hot start PCR are described in D'Aquila, R. T., et al. which is incorporated herein by reference(25, 26, 31, 32). The direct hot start PCR of this invention may be carried out in accordance with general procedures and conditions for hot start PCR known to one skilled in the art, except that a biological specimen is directly used instead of isolated nucleic acid and a zwitterionic buffer and/or a non-reducing carbohydrate are used in the reaction mixture.

The biological specimen used in the present invention is not limited, preferably, includes virus, bacteria, tissue, cell, blood, lymph, myeloid fluid, saliva, milk, urine, feces, ocular fluid, semen, brain extracts, spinal cord fluid, joint fluid, thymic fluid, ascitic fluid, amniotic fluid and cell tissue fluid, more preferably, virus, bacteria, tissue, cell, blood, saliva, milk, urine and feces, still more preferably, virus, bacteria, tissue, cell and blood, and most preferably, blood. As a biological specimen, blood may be whole blood, plasma or serum, preferably, whole blood sample.

It is preferred that the whole blood is pretreated with anticoagulants such as heparin, EDTA (ethylene diaminetetraacetic acid) and sodium citrate prior to the addition to the reaction mixture. However, anticoagulants are very likely to inhibit an enzyme reaction, in particular, PCR activity, so that they become a limiting factor in determining the amount of blood added into PCR reactions. The present invention using a zwitterionic buffer and/or a non-reducing carbohydrate can overcome such drawback derived from anticoagulants, allowing for the use of larger amount of blood in the direct amplification, e.g., up to 10% (v/v) relative to the total volume of reaction mixtures as demonstrated in Example III.

The most striking feature of this invention is to use a zwitterionic buffer and/or a non-reducing carbohydrate serving as an agent for preventing biological specimens from inhibiting enzymatic reactions. Various substances (e.g., heme, immunoglobulin G, inorganic salts, bile salts, DNases and proteinases) present in biological specimens inhibit the activity of enzymes involved in reactions. The present inventors have found that a zwitterionic buffer and/or a non-reducing carbohydrate could overcome obstacles originated from biological specimen-containing substances that inhibit enzymes involved in reactions. Such great achievement of this invention can be made with the help of a zwitterionic buffer or a non-reducing carbohydrate alone. Preferably, the instant invention uses both zwitterionic buffer and non-reducing carbohydrate.

The term "zwitterionic buffer" used herein means a buffer comprising a compound with acidic and basic groups in the same molecule. At neutral pH most zwitterionic buffers have therefore negatively charged anions and positively charged cations at the same time. Zwitterionic buffers are sometimes referred to as "Good" buffers(33). Any zwitterionic buffer known to one skilled in the art may be used in this invention, including, preferably, HEPES (4-(2-Hydroyethyl)-1-piperazineethanesulfonic acid), Tricine (N-Tris(hydroxymethyl) methylglycine), Bicine (NN-bis(2-hydroxyethyl)glycine), Taps (N-Tris(hydroxymethyl)methyl-3-aminopropanesulphonic acid), ACE (N-(2-acetamido)-2-aminoethane-sulfonic acid), ADA (N-(2-acetamido)-iminodiacetic acid), MES (2-(N-morpholino)-ethanesulfonic acid), MOPS (3-(N-morpholino)propanesulfonic acid) and MOPSO (3-N-morpholino)-2-hydroxypropanesulfonic acid), MOPSO (3-[N-Morpholino]-2-hydroxypropanesulphonic acid), PIPES (piperazine-1,4-bis(2-ethanesulfonic acid)) and CAPS(N-Cyclohexyl-3-aminopropanesulfonic acid), more preferably, HEPES, Tricine and Bicine, and most preferably, Tricine.

The concentration of zwitterionic buffers used in this invention is not particularly limited, preferably, 5-60 mM, more preferably, 10-60 mM, and most preferably, 10-50 mM. The pH of the reaction mixture adjusted by zwitterionic buffers varies depending on a number of reaction conditions such as the type of enzymes used, preferably, ranging from 6.8-9.5, more preferably, 7.5-9.0, most preferably, 8.0-8.7.

The feature of this invention to ensure the direct enzymatic reaction can be accomplished solely using a non-reducing carbohydrate.

The term "non-reducing carbohydrate" used herein refers to a hydrocarbon having no less than two hydroxyl groups and not having a reducing power. The non-reducing carbohydrate includes polyols (polyhydroxy compounds) and their derivatives. Representative examples of polyols include glycols, polyglycols (e.g., polyethylene glycol) and polyglycerols. In addition, representative examples of the non-reducing carbohydrate include non-reducing hydrates of carbon, called non-reducing sugars or saccharides, and their derivatives. Exemplified non-reducing sugars include, but not limited to, disaccharides such as sucrose, trehalose and palatinitol, trisaccharides such as raffinose and melezitose, tetrasaccharides such as stachyose. The non-reducing sugar derivatives include, but not limited to, sugar alcohols (the hydrogenated forms of aldoses or ketoses) such as sorbitol, mannitol, erythritol and xylitol (derived from monosaccharides), lacitol and maltitol (derived from disaccharides); aldonic acids and their lactones such as gluconic acid, gluconic acid $\gamma$-lactone; aldaric acids and their lactones such as ribaraic acid, arabinaric acid and galactaric acid; uronic acid such as glucuronic acid, galaccuronic acid and mannuronic acid; ester derivatives (preferably, $C_1$-$C_4$ fatty acid ester derivatives) such as trehalose octaacetate, sucrose octaacetate, and cellobiose octaacetate; and ether derivatives (preferably, $C_1$-$C_4$ alkyl ether derivatives) in which hydroxyl groups are converted into ethers. Both D and L forms of the non-reducing carbohydrates may be used.

Preferably, the non-reducing carbohydrate useful in this invention includes non-reducing disaccharides, trisaccharides, tetrasaccharides, and sugar alcohols derived from monosaccharides, more preferably, non-reducing disaccharides and sugar alcohols derived from monosaccharides, and most preferably, sorbitol, mannitol, trehalose, raffinose and sucrose.

The amount of non-reducing carbohydrates used in this invention is not particularly limited, preferably, at least 1.5% (w/v), more preferably, at least 2% (w/v), and most preferably, 2-30% (w/v), based on the total weight of the reaction mixture.

According to a preferred embodiment, the present invention is applied to nuclease-mediated reactions. More preferably, the present invention is performed following the Invader assay(34-36) (U.S. Pat. Nos. 5,846,717, 6,090,543, 6,001, 567, 5,985,557 and 5,994,069). In the direct Invader assay directly using biological specimens, a zwitterionic buffer and/or a non-reducing carbohydrate prevents biological specimens from inhibiting enzymatic reactions such as FEN-1 endonuclease-mediated reaction. The Invader assay detects specific DNA and RNA sequences by using structure-specific enzymes such as FEN-1 endonuclease to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. The secondary probe oligonucleotide can be 5'-end labeled with a fluorescent dye that is quenched by a second dye or other quenching moiety. Upon cleavage, the de-quenched dye-labeled product may be detected using a standard fluorescence plate reader, or an instrument configured to collect fluorescence data during the course of the reaction. The Invader assay detects specific mutations and SNPs (single nucleotide polymorphisms) in unamplified genomic DNA. The Invader assay may be combined with multiplex PCR for genome-wide association studies(36).

The reaction mixture used in this invention may further comprise a zwitterionic surfactant, a bovine serum albumin, a polyamine or their combination. These additives also are able to prevent biological specimens from inhibiting enzymatic reactions. However, it is unnecessary in this invention to use these additives for performing direct enzymatic reactions. The zwitterionic surfactant useful in this invention includes, not limited to, n-octyl-N,N-dimethyl-3-ammonio-1-propanesulfonate, n-decyl-N,N-dimethyl-3-ammonio-1-propanesulfonate, n-dodecyl-N,N-dimethyl-3-ammonio-1-propanesulfonate, n-tetradecyl-N,N-dimethyl-3-ammonio-1-propanesulfonate, n-hexadecyl-N,N-dimethyl-3-ammonio-1-propanesulfonate, CHAPS (3-[(3-cholamidopropyl)dimethylammonio]-1-propanesulfonate) and zwittergent (N-alkyl-N,N-dimethyl-3-ammonio-1-propane-sulfonate), preferably, CHAPS and zwittergent, more preferably, CHAPS. The polyamine useful in this invention is not limited, including preferably, spermine, putrescine, spermidine and triethylenetetramine, more preferably, spermidine and triethylenetetramine, and most preferably, triethylenetetramine.

The advantages of the present invention become most highlighted when it is applied to directly amplify nucleic acid molecules having low copy number present in biological specimens, in particular, blood. The term "low-copy number" with reference to nucleic acid molecule as templates refers to 1-1000 copies of target nucleic acid molecules. There have not yet been reported the direct amplification using biological specimens of nucleic acid molecules in low copy number. Surprisingly, the present invention can directly amplify HIV-1 nucleic acid in low copy number (e.g., 10 copies of HIV-1 nucleic acid in 50 µl total reaction) using blood samples, as demonstrated in Example V.

The present invention is directed to a novel approach to enable the direct enzymatic reaction (preferably, amplification, more preferably, PCR-based amplification) to be practicable by overcoming obstacles derived from enzyme inhibitors present in biological specimens. To our best knowledge, the achievements in this invention are the most excellent compared to other direct amplification processes reported so far such as methods of Nishimura et al. (U.S. Pat. Nos. 5,935, 825 and 6,413,747) and Al-Soud et al. (16, 37).

More particularly, the methods of Nishimura et al. have serious problems in which chemical-modified polymerases for hot start PCR such as AmpliTaq Gold DNA polymerase (Applied Biosystems, Inc.), FastStart Taq DNA polymerase (Roche Applied Science, Inc.) and HotStarTaq DNA polymerase (Qiagen, Inc.) do not work under conditions suggested by Nishimura et al. In addition, the attempts of Al-Soud et al. cannot give amplification results for a DNA template in low copy number. In contrast to these conventional techniques, the present invention exhibits improved performance in nearly all amplification reactions.

The method of Nishimura et al. uses Tris(hydroxyamino)methane (Tris) reaction buffer (10 mM Tris-HCl, above pH 8.9 at 25° C., 50 mM KCl), providing a strategy to defy PCR inhibition by increasing pH to above that of general PCR reaction buffer. By contrast, the present invention overcomes completely the PCR inhibition due to biological specimen by using a zwitterionic buffer (or Good buffer, pH 8.3-8.9 at 25° C.) and/or a non-reducing carbohydrate. As described hereunder in Examples, the PCR reactions of this invention for amplifying target nucleic acid molecules in blood show very excellent action to prevent PCR inhibition, even at lower pH than Tris buffer-using technologies.

Furthermore, Nishimura et al. have reported results obtained by using only Taq DNA polymerase. Reports relating to Ampdirect™ of Shimadzu, Inc. suggest no success in the blood-using direct amplification by use of Pfu DNA polymerase. Unlikely, the direct amplification of the present invention is able to perform using a wide variety of thermostable polymerases including Tth DNA polymerase, Pfu DNA polymerase and Pwo DNA polymerase as well as Taq DNA polymerase.

AmpFLSTR® Identifiler® kit (Applied Biosystems, Inc.) is most widely employed for gene testing or identification. When blood samples are directly applied to this kit, amplification products are not generated. However, where the zwitterionic buffer and/or non-reducing carbohydrate are added to the reaction mixture, the kit produced analysis results of interest as demonstrated in Example IX. In addition, according to the present invention, a bloodstain on Guthrie card, FTA card or filter paper can be directly used as templates for the direct gene testing.

The present invention is also directed to a kit for performing a direct enzymatic reaction. The present kit for performing a direct enzymatic reaction may optionally include other components required for performing enzymatic reactions such as enzymes, substrates and cofactors. Where the kit of this invention is constructed for amplifying DNA molecules, it may optionally include the reagents required for performing PCR reactions such as DNA polymerase, cofactors, and deoxyribonucleotide-5-triphosphates (dNTPs). Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The kits, typically, are adapted to contain in separate packaging or compartments the constituents afore-described.

In still another aspect of this invention, there is provided a method for preventing a biological specimen from inhibiting an enzymatic reaction involving a nucleic acid molecule, which comprises contacting to the biological specimen a reaction mixture for the enzymatic reaction containing a zwitterionic buffer and/or a non-reducing carbohydrate, wherein a nucleic acid molecule present in the biological specimen is not purified before the enzymatic reaction.

In further aspect of this invention, there is provided a use of a zwitterionic buffer and/or a non-reducing carbohydrate for manufacturing a reaction mixture for a direct enzymatic reaction involving a nucleic acid molecule.

Since these aspects of this invention follow the principles of the method of this invention described hereinabove, the common descriptions between them are omitted in order to avoid undue redundancy leading to the complexity of this specification.

Nucleic acid purification (isolation) considered to be tedious is a time- and cost-consuming procedure and usually employs toxic materials such as phenol. This procedure may also induce some problems: (i) infection to researchers; (ii) cross-contamination between nucleic acid samples; and (iii) loss of nucleic acid, in particular, when trace amount of sample is present. Therefore, there remains a long-felt need to develop the direct enzymatic reaction (particularly, amplification reaction) without nucleic acid purification. In addition, for comparison experiments using many samples, nucleic acid purification is very likely to give rise to artifact errors due to variation in the purification efficiency. It could be therefore understood that using biological specimen without nucleic acid purification can eradicate such artifact errors.

According to the present invention, the automation of enzymatic reactions (particularly, amplification reactions) can be readily constructed due to simple preparation of samples, and even trace amount of samples can be enzymatically processed. In addition to this, the present invention permits to cope with acute situations because of its time effectiveness, producing prompt amplification results, and allows for conducting outdoor analysis in easy manner because of no need for devices and reagents for nucleic acid purification.

The following specific examples are intended to be illustrative of the invention and should not be construed as limiting the scope of the invention as defined by appended claims.

EXAMPLES

The percentages given below for solid in solid mixture, liquid in liquid, and solid in liquid are on a w/w, v/v and w/v basis, respectively, unless specifically indicated otherwise.

Example I

Nucleic Acid Amplification Using Blood Samples (with Various Types of Buffers)

PCR reactions involving Taq DNA polymerase generally use 10× concentrated PCR buffers (containing 100 mM Tris-HCl, 500 mM KCl and 15 mM $MgCl_2$) of which pH adjusted by Tris's buffering power is predominantly 8.3 and may increase up to 9.0.

In order to verify that a Good buffer is responsible for preventing blood samples from inhibiting a PCR activity, 10× concentrated PCR buffers containing 100 mM buffer (Tris or Good, such as Tricine, HEPES and Bicine), 500 mM KCl and 15 mM $MgCl_2$ were prepared and PCR reactions were carried out directly using blood samples. The pH of Tris-buffer was adjusted from 8.3 to 9.0 (increased by 0.1), those of Tricine-buffer and HEPES-buffer from 8.0-9.0 (increased by 0.1) and that of Bicine-buffer from 8.0-8.8 (increased by 0.1). The pHs of buffers were measured at 25° C.

The PCR reactions were carried out using 50 μl total volume of PCR reaction mixtures containing 5 μl of 10× concentrated PCR buffer, 0.2 mM dNTPs mixture and 0.4 μM primers, GH2O (sense primer, 5'-CAACTTCATCCACGT-TCACC-3') (SEQ ID NO:1) and GH21 (antisense primer, 5'-GGAAAATAGACCAATAGGCAG-3') (SEQ ID NO:2) for human β-globin(3). AmpliTaq DNA polymerase (5 unit/μl Applied Biosystems, Inc.) and 1 μl of heparin-pretreated blood samples were used for direct PCR. The PCR reactions were conducted under the following thermal conditions: 10 min at 94° C. followed by 40 cycles of 30 sec at 94° C., 30 sec at 55° C., and 1 min at 72° C.; followed by a 7 min final extension at 72° C. The initial denaturation step at 94° C. for 10 min was employed to disrupt cells and denature PCR inhibitors such as proteinases and DNases present in blood samples. Amplified products were analyzed by electrophoresis on a 2% agarose gel containing 0.5 μg/ml ethidium bromide and subsequent UV radiation.

FIG. 1 shows the amplification results of 408 bp β-globin using a primer set GH20/GH21. Although Tris-buffer generates PCR products only when its pH becomes no less than 8.5 (lanes 3-9), a Good buffer shows PCR products even at a lower pH, i.e., pH 8.3 for Tricine-buffer (lane 12), pH 8.1 for Bicine-buffer (lane 22) and pH 8.0 for HEPES-buffer (lane 30). Therefore, it could be appreciated that a Good buffer successfully prevents blood samples from inhibiting PCR activity.

Figure 2:
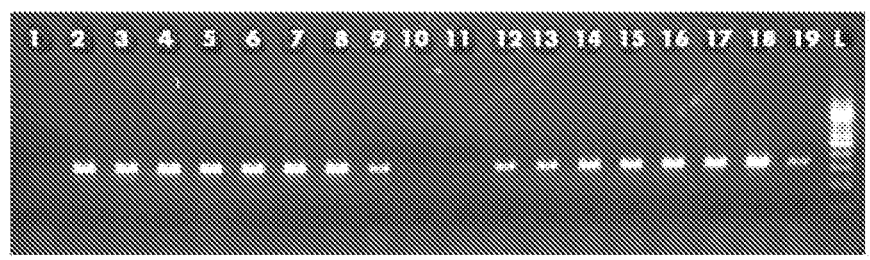
FIG. 2 shows the direct PCR results of the β-globin gene (325 bp) using a primer set GH20/KM38. Lanes 1-9 correspond to Tricine-buffer (pH 8.0, 8.3, 8.4, 8.5, 8.6, 8.7, 8.8, 8.9 and 9.0, respectively), and lanes 10-19 to Tris-buffer (pH 8.3, 8.4, 8.5, 8.6, 8.7, 8.8, 8.9, 9.0, 9.2 and 9.5, respectively). L denotes a 100 bp ladder ranging from 100 to 1500 bp.

FIG. 2 represents the amplification results of 325 bp globin using a primer set GH2O/KM38 (KM38 primer, 5'-TG-GTCTCCTTAAACCTGTCTTG-3') (SEQ ID NO:3). The PCR conditions are the same as those for GH20/GH21 primer set. Similar to results of FIG. 1, the amplifications using Tris-buffers having pH of less than 8.5 are shown to be inhibited by blood samples; however, a Good buffer, Tricine-buffer having pH 8.3 allows for direct PCR amplifications using blood samples.

Figure 3:
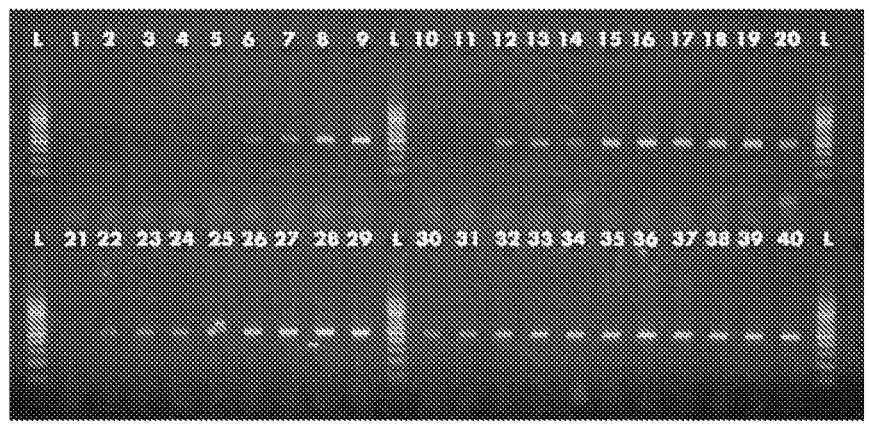
FIG. 3 shows the direct PCR results of the p53 gene. Lanes 1-9 represents the results using Tris-buffer (pH 8.3, 8.4, 8.5, 8.6, 8.7, 8.8, 8.9, 9.0 and 9.2, respectively), lanes 10-20 using Tricine-buffer (pH 8.0, 8.1, 8.2, 8.3, 8.4, 8.5, 8.6, 8.7, 8.8, 8.9 and 9.0, respectively), lanes 21-29 using Bicine-buffer (pH 8.0, 8.1, 8.2, 8.3, 8.4, 8.5, 8.6, 8.7 and 8.8, respectively), and lanes 30-40 using HEPES-buffer (pH 8.0, 8.1, 8.2, 8.3, 8.4, 8.5, 8.6, 8.7, 8.8, 8.9 and 9.0, respectively). L denotes a 100 bp ladder ranging from 100 to 1500 bp.

The p53 gene was amplified using a sense primer (E6f, 5'-TGTTCACTTGTGCCCTGACT-3') (SEQ ID NO:4) and an antisense primer (E6r, 5'-GGAGGGCCACTGA-CAACCA-3') (SEQ ID NO:5) to obtain 489 bp PCR products. The 50 μl PCR mixture contains 0.2 mM dNTPs mixture, 0.4 μM primers, 0.4 μl AmpliTaq DNA polymerase and 1 μl heparin-treated blood sample. The PCR reactions were conducted under the following thermal conditions: 10 min at 94° C. followed by 40 cycles of 30 sec at 94° C., 30 sec at 56° C., and 1 min at 72° C.; followed by a 7 min final extension at 72° C. Amplified products were resolved by electrophoresis on a 2% agarose gel. As shown in FIG. 3, Tris-buffer involved amplifications become to generate weak bands from pH 8.8 and strong bands at pH 9.0 and 9.2. Unlikely, Tricine-, Bicine- and HEPES-buffers produce PCR amplification bands at a much lower pH.

HEPES-buffer produces better results in a broad pH range, as observed in FIGS. 1 and 3. The reason for that is that PCR reactants such as dNTPs and primers are added to HEPES buffer having pH of more than 8.3 to induce a sharp pH decrease around pH 8.3 in the PCR mixture due to the buffering region of HEPES (pH 6.8-8.2), which contributes to similar PCR results at varying pH values.

The action of PCR inhibitors present in blood has to be blocked for successful direct amplifications. The present inventors reasoned that the action of a representative inhibitor in blood, hemoglobin could be blocked by intermolecular binding of hemoglobin under denaturation-inducible pH and temperature conditions. We adopted such reasoning to select a type of suitable buffers for promising direct amplifications.

Nishimura et al. have reported that a higher pH is responsible for direct PCR amplification using blood samples. However, it would be understood that the excellent results using Good buffers are not due to higher pH values of PCR mixtures containing Good buffer in the senses that Tricine buffer produces PCR amplicons from blood samples at low pH despite of the fact that Tricine buffer exhibits large pH changes depending on temperature compared to other Good buffers (Tricine: ΔpKa/° C. −0.021, Bicine: ΔpKa/° C. −0.018, HEPES: ΔpKa/° C. −0.014, from Merck Index). It has been known that pH of Tris buffer is decreased by 0.03 at 5-25° C. and by 0.025 at 25-37° C. (publications from Sigma, Inc.).

We employed some properties of Good buffers including amphoteric buffer, unreactivity, and low ionic strength rather than their pH ranges. Unlikely to Tris buffer, Good buffers bear both positive and negative charges so that they are capable of binding to biomolecules with either positive or negative charges. In addition, we recognized that Good buffers could enhance a heat denaturation of proteins owing to their low ionic strength. The precipitation of protein is induced at pH of around pI and promoted at low ionic strength. Therefore, these facts led us to reason that PCR reactions containing Good buffers become to have low ionic strength, their pH values become to be around pI of PCR inhibiting proteins upon temperature elevation, which induces agglutination of proteins in blood samples to block the actions of PCR inhibitors.

Example II

Nucleic Acid Amplification Using Blood Samples (with Various Types of Additives)

To investigate the effect of additives on direct amplification using blood samples, PCR amplifications were conducted using non-reducing carbohydrate, surfactants or other known conventional additives (e.g., polyamine, BSA and betaine) for general PCR process.

Example II-1

Effect of Non-Reducing Carbohydrates

To elucidate the positive effect of non-reducing carbohydrates and their derivatives on direct amplification, PCR using non-isolated DNA as a template contained in blood samples was carried out to amplify p53. The primers and conditions used are the same as those of Example I, except that Tricine-buffer (pH 8.3) was used.

Figure 4:
FIG. 4 represents analysis results on the potential of various non-reducing carbohydrates to prevent blood samples from inhibiting amplification reactions: Glucose (panel A, lanes 3-6), sucrose (panel A, lanes 7-10), lactose (panel A, lanes 11-14), melezitose (panel A, lanes 15-18), stachylose (panel A, lanes 19-22), trehalose (panel B, lanes 3-6), raffinose (panel B, lanes 7-10), sorbitol (panel B, lanes 11-14), mannitol (panel B, lanes 15-18) and polyvinylpyrrolidone (panel B, lanes 19-22). In panel A and B, lane 1 corresponds to no addition of non-reducing carbohydrates, and lane 2 to the result using 2 ng human genomic DNA instead of blood.

As shown in FIG. 4, PCR amplification using glucose (panel A, lanes 3-6, 0.18, 0.38, 0.75 and 1.5% (w/v), respectively) shows no amplicons. Similar to this, lactose (panel A, lanes 11-14, 0.18, 0.38, 0.75 and 1.5% (w/v), respectively) also fails to amplify the p53 gene at higher concentrations, while its lower concentrations show weak product bands. It would be appreciated that lactose at low concentration could not contribute to the success of direct amplification using blood upon comparing to the control band (panel A and B, lane 1) and even inhibits a direct PCR activity at its higher concentrations. These results lead us to reason that reducing carbohydrates fails to enable the direct amplification using biological specimens containing inhibitors to amplification.

As a representative in non-reducing sugars, sucrose (FIG. 4, panel A, lanes 7-10, 1.25, 2.5, 5 and 10% (w/v), respectively), trehalose (FIG. 4, panel B, lanes 3-6, 0.94, 1.8, 3.8 and 7.5% (w/v), respectively) and raffinose (FIG. 4, panel B, lanes 7-10, 0.87, 1.8, 3.5 and 7% (w/v), respectively) were tested to verify their potential to prevent blood samples from inhibiting amplification reactions. The reducing sugars exhibit an increasing prevention potential upon increasing their concentration. In addition, it was revealed that other non-reducing sugars such as melezitose (FIG. 4, panel A, lanes 15-18, 0.6, 1.25, 2.5 and 5% (w/v), respectively) and stachyose (FIG. 4, panel A, lanes 19-22, 0.6, 1.25, 2.5 and 5% (w/v), respectively) also prevent blood samples from inhibiting amplification reactions.

The accomplishment of direct amplifications using blood samples also was observed in alditols (sugar alcohols) having no reducing power including sorbitol (FIG. 4, panel B, lanes 11-14, 1.25, 2.5, 5 and 10% (w/v), respectively) and mannitol (FIG. 4, panel B, lanes 15-18, 0.6, 1.25, 2.5 and 5% (w/v), respectively).

Meanwhile, polyvinyl pyrrolidone (FIG. 4, panel B, lanes 19-22, 0.25, 0.5, 1 and 2% (w/v), respectively) which does not fall within the definition of non-reducing carbohydrates described herein, fails to allow for the direct amplification using blood samples.

Consequently, these results demonstrate that non-reducing carbohydrates serve as an excellent agent for permitting the direct amplification using biological specimens containing inhibitors against amplification.

Example II-2

Detailed Evaluation on Effect of Trehalose and Raffinose

To investigate in more detail the effect of trehalose (as a representative of disaccharide) and raffinose (as a representative of trisaccharide) on direct amplification, PCR amplifications using unpurified DNA as a template contained in blood samples were carried out to amplify p53. The primers and conditions used are the same as those of Example I, except that either Tris-buffer (pH 8.3) or Tricine-buffer (pH 8.3) was used and 2.5 µl of heparin-pretreated blood samples (5% (v/v) relative to the total volume of PCR reactions) was used.

Figure 5:
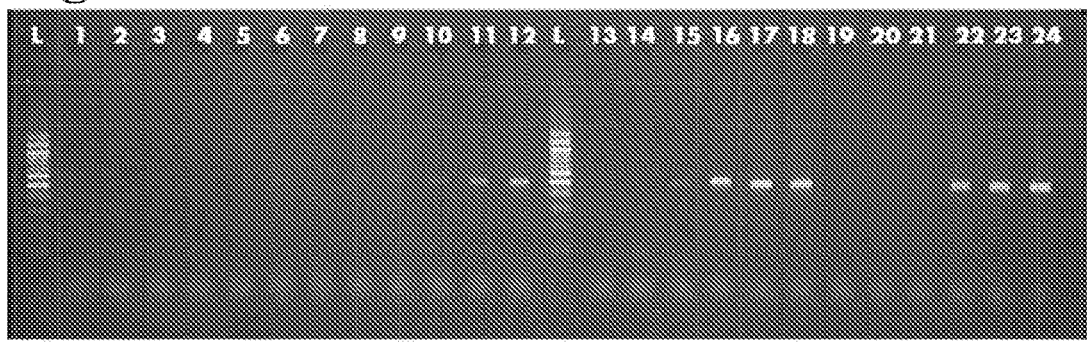
FIG. 5 shows the direct PCR results using raffinose or trehalose as agents for preventing blood samples from inhibiting amplification reactions. Either Tris-buffer (pH 8.3) (lanes 1-12) or Tricine-buffer (pH 8.3) (lanes 13-24) was used. The final concentrations (% (w/v)) of raffinose are 0 (lanes 1 and 13), 1.4 (lanes 2 and 14), 2.8 (lanes 3 and 15), 4.2 (lanes 4 and 16), 5.6 (lanes 5 and 17), and 7.0 (lanes 6 and 18). Trehalose was used at the final concentrations (% (w/v)) of 1.5 (lanes 8 and 20), 3.0 (lanes 9 and 21), 4.5 (lanes 10 and 22), 6.0 (lanes 11 and 23) and 7.5 (lanes 12 and 24).

As shown in FIG. 5, conventional PCR reactions (lanes 1 and 13) using 5% blood sample and 2.0 unit Taq DNA polymerase without non-reducing carbohydrates are inhibited by blood samples. Where Tris-buffer is used, 7% raffinose shows very weak band (lane 6) and trehalose exhibits more evident bands upon increasing its concentration (lanes 8-12). Unlikely, both raffinose and trehalose in Tricine-buffer show evident amplification bands at their relatively high concentrations (lanes 16-18 and 22-24).

Figure 6:
FIG. 6 shows the direct PCR results using trehalose as agents for blocking the action of blood samples to inhibit amplification reactions. Tricine-buffer (pH 8.3) and 2.0 unit AmpliTaq DNA polymerase were used. The final concentrations of trehalose used in lanes 1-8 are 0, 2.4, 4.8, 6, 12, 18, 24 and 30% (w/v), respectively.
Figure 7:
FIG. 7 represents analysis results on the trehalose effect on direct amplification reactions depending on pH. Lanes 1-9 correspond to Tris-buffer (pH 8.3, 8.4, 8.5, 8.6, 8.7, 8.8, 8.9, 9.0 and 9.2, respectively), and lanes 10-20 to Tricine-buffer (pH 8.0, 8.1, 8.2, 8.3, 8.4, 8.5, 8.6, 8.7, 8.8, 8.9 and 9.0, respectively). 1 unit of AmpliTaq DNA polymerase was used. Panel A represents 0% trehalose and panel B represents 3% (w/v) trehalose.

Furthermore, the trehalose effect was confirmed using its increasing concentrations (0-30% (w/v)) as represented in FIG. 6. Such trehalose effect was revealed to exhibit more clearly in parallel with increasing its concentrations.

Accordingly, it could be appreciated that non-reducing carbohydrates can completely avoid the actions of inhibitors contained in blood samples, thereby rendering the direct amplification using biological specimens true.

Figure 8:
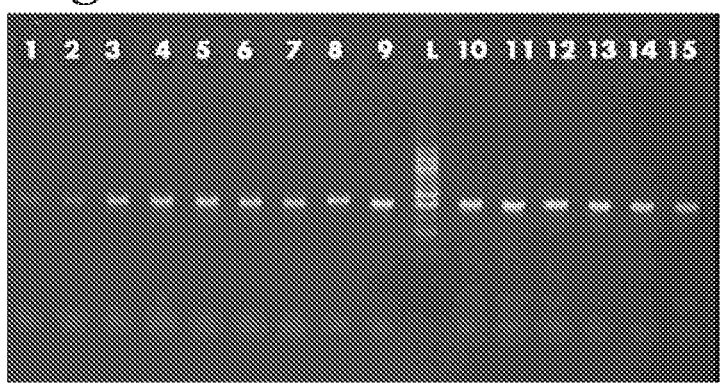
FIG. 8 shows the direct PCR results for amplifying the p53 gene using CHAPS. Tricine-buffer (pH 8.3) (lanes 1-9) or Tricine-buffer (pH 8.7) (lanes 10-15) was used. A total 50 μl PCR reactions including 0.4 mM triethylenetetramine (lane 2) or 2.4% trehalose (lanes 3-15) were used. The concentrations of CHAPS are 0 mM (lanes 1, 2 and 3), 0.3 mM (lanes 4 and 10), 0.6 mM (lanes 5 and 11), 1.25 mM (lanes 6 and 12), 2.5 mM (lanes 7 and 13), 5 mM (lanes 8 and 14), and 10 mM (lanes 9 and 15).

To investigate the combined effect of buffers (pH and types) and non-reducing carbohydrates, Tris-buffer (pH 8.3-9.0 and 9.2) or Tricine-buffer (pH 8.0-9.0) in the presence or absence of trehalose was used for directly amplifying p53. The primers and conditions used are the same as described above, except that 1.0 unit Taq DNA polymerase was used. Where additives were not employed, the PCR amplified products were observed only at much higher pH (e.g., above pH 9.0) for Tris-buffer but were observed at relatively lower pH (e.g., above 8.6) for Tricine-buffer (FIG. 8, panel A). In the case that 3% (w/v) trehalose was added in PCR reactions, pH at which generates amplified products becomes lower: above pH 8.5 for Tris-buffer and above pH 8.2 for Tricine-buffer (FIG. 8, panel B).

Therefore, it could be understood that non-reducing carbohydrates combined with a suitable buffer type and pH exert much greater capacity to prevent biological specimens from inhibiting amplification reactions.

Example II-3

Effect of Surfactants

We tested whether zwitterionc surfactants such as CHAPS (3-[(3-cholamidopropyl)dimethylammonio]-1-propane-sulfonate) can improve direct amplification reactions using blood samples. PCR reactions for amplifying p53 were conducted in the same manner as described in Example I. As shown in FIG. 8, CHAPS in Tricine-buffer (pH 8.3 or 8.7) promotes direct amplifications using blood samples in the concentration-dependent manner.

Example II-4

Effect of Polyamines

Spermidine as a representative of polyamines has been reported to increase the efficiency of PCR amplification. Kato et al. addressed that polyamines in a high concentration could avoid the actions of PCR inhibitors contained in blood, urine and feces (U.S. Pat. No. 6,413,747).

PCR reactions for amplifying p53 were carried out to compare the polyamine effects in Tris buffers and Good buffers. The varying concentration of spermidine or triethylenetetramine and 2% (v/v) heparin-treated blood were used. The primers and conditions for PCR reactions are the same as described in Example I.

Figure 9:
FIG. 9 shows the direct PCR results for amplifying the p53 gene using polyamines, spermidine (panel A) and triethylenetetramine (panel B). 1 µl of heparin-treated blood was directly used. Lanes 1-6 correspond to Tris-buffer (pH 8.3), lanes 7-12 to Tricine-buffer (pH 8.3), lanes 13-18 to Tris-buffer (pH 8.7), and lanes 19-24 to Tricine-buffer (pH 8.7). The final concentrations of spermidine or triethylenetetramine are 0 mM (lanes 1, 7, 13 and 19), 0.25 mM (lanes 2, 8, 14 and 20), 0.5 mM (lanes 3, 9, 15 and 21), 1.0 mM (lanes 4, 10, 16 and 22), 2.0 mM (lanes 5, 11, 17 and 23), 4 mM (lanes 6, 12, 18 and 24).
Figure 10:
FIG. 10 shows the direct PCR results using Tricine-buffer (at pH 8.3 in lanes 1-12, at pH 8.7 in lanes 13-24) containing different concentrations of spermidine (lanes 1-6 and 13-18) or triethylenetetramine (lanes 7-12 and 19-24). 2 µl of heparin-treated blood were directly used. The final concentrations of spermidine or triethylenetetramine are 0 mM (lanes 1, 7, 13 and 19), 0.25 mM (lanes 2, 8, 14 and 20), 0.5 mM (lanes 3, 9, 15 and 21), 1.0 mM (lanes 4, 10, 16 and 22), 2.0 mM (lanes 5, 11, 17 and 23), 4 mM (lanes 6, 12, 18 and 24).

As represented in FIG. 9, all concentrations (even 4 mM) of spermidine and triethylenetetramine produce no amplicon in Tris-buffer at pH 8.3 (lanes 1-6), while spermidine and triethylenetetramine show increased PCR products to their concentrations of 0.5 mM and 1 mM, respectively, in Tris-buffer at pH 8.7 (lanes 13-18). Meanwhile, it was difficult to evaluate the polyamine effect in PCR using Tricine-buffer at pH 8.3 or 8.7. A higher concentration of polyamines in Tris- and Tricine-buffer even inhibited PCR activity. In experiments using 4% (v/v) heparin-treated blood, the positive effect of polyamines on PCR using blood samples was observed in Tricine-buffer as shown in FIG. 10.

Example II-5

Effect of BSA

Kreader(12) and Al-Soud et al. (16, 37) suggested that a high concentration of BSA could prevent blood samples from inhibiting PCR. PCR reactions for amplifying p53 were carried out to examine such BSA effects in Tris buffers and Good buffers, and used 2% (v/v) heparin-treated blood. The primers and conditions for PCR reactions are the same as described in Example I.

Figure 11:
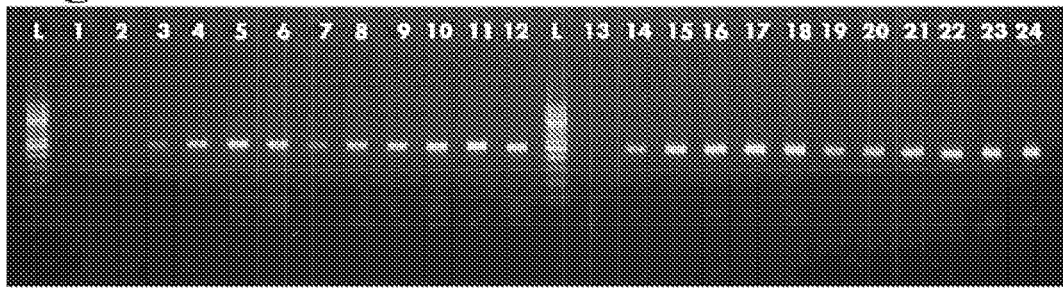
FIG. 11 shows the direct PCR results for amplifying the p53 gene using different concentrations of BSA (bovine serum albumin). Lanes 1-6 correspond to Tris-buffer (pH 8.3), lanes 7-12 to Tricine-buffer (pH 8.3), lanes 13~18 to Tris-buffer (pH 8.7), and lanes 19-24 to Tricine-buffer (pH 8.7). The final concentrations of BSA are 0 mg/ml (lanes 1, 7, 13 and 19), 0.62 mg/ml (lanes 2, 8, 14 and 20), 1.25 mg/ml (lanes 3, 9, and 21), 2.5 mg/ml (lanes 4, 10, 16 and 22), 5 mg/ml (lanes 5, 11, 17 and 23), and 10 mg/ml (lanes 6, 12, 18 and 24).

As represented in FIG. 11, PCR reactions containing BSA in Tris-buffer at pH 8.3 or 8.7 generated p53 amplicons; in the case of not using BSA, no p53 amplicon (lanes 1 and 13). In contrast, the amplification reactions without or containing BSA in Tricine-buffer at pH 8.3 or 8.7 produced p53 amplicons. In particular, it was clearly observed that the BSA effect was exerted more evidently upon increasing its concentration in Tricine-buffer at pH 8.3.

Therefore, it would be recognized that where BSA is further added into amplification reactants, the direct amplification using the present buffer system with zwitterionic buffers can be performed with higher efficiency.

Al-Soud et al. described that the BSA effect is ascribed to protecting DNA polymerase against the action of proteinases and preventing heme group from binding to Taq polymerase. However, considering that Tris-buffer at higher pH and Tricine-buffer at pH 8.3 enables a direct PCR using blood samples, the BSA effect is expected to be due to its ability to prevent heme group rather than its protection ability against proteinases. In addition, it could be suggested that the denatured form of BSA at high temperature may induce easily the aggregation of proteins involving in the inhibition to PCR activity, to decrease the inhibitory action of the proteins.

Example III

Analysis of Effect of Anticoaggulants

Blood samples for amplification are generally prepared by the pretreatment with anticoagulants including heparin, EDTA and sodium citrate. However, these anticoagulants are very likely to inhibit PCR activity, so that they become a limiting factor in determining the amount of blood added into PCR reactions.

PCR reactions using Good buffers for amplifying p53 were carried out to evaluate a suitable blood amount in our direct amplification reaction system. The primers and conditions for PCR reactions are the same as described in Example I.

Figure 12:
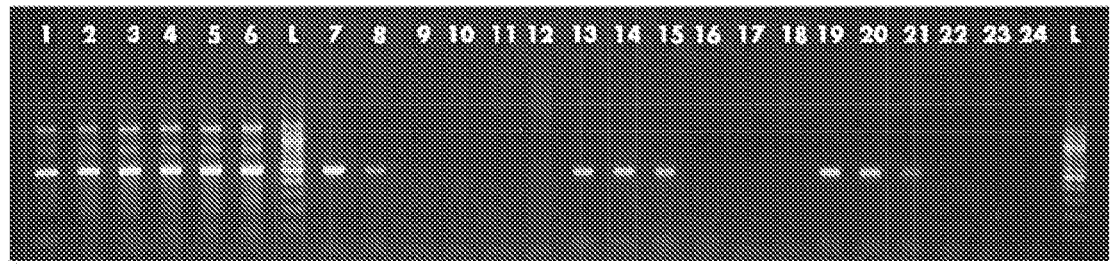
FIG. 12 represents the PCR results for amplifying the p53 gene using different templates. Lanes 1-6 correspond to a human genomic DNA (0.3, 0.6, 1.25, 2.5, 5 and 10 ng, respectively), lanes 7-12 to heparin-treated blood (0.6, 1.25, 2.5, 5, 10 and 20 µl, respectively), lanes 13-18 to EDTA-treated blood (0.6, 1.25, 2.5, 5, 10 and 20 µl, respectively), and lanes 19-24 to sodium citrate-treated blood (0.6, 1.25, 2.5, 5, 10 and 20 µl, respectively). Tricine-buffer (pH 8.7) was used.
Figure 13:
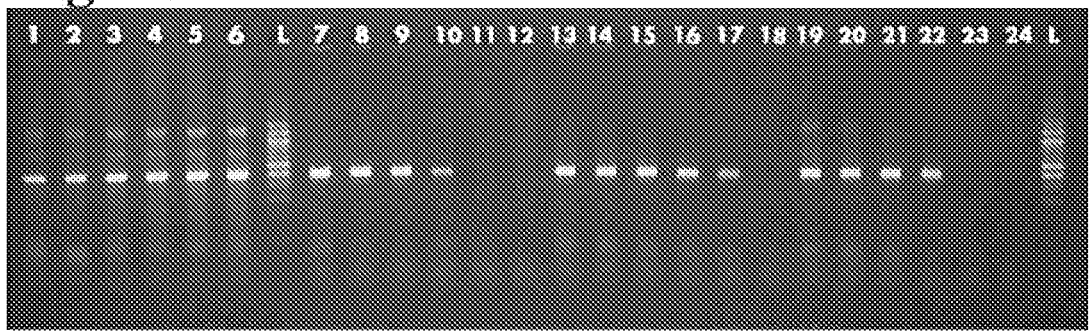
FIG. 13 represents the PCR results for amplifying the p53 gene using different templates. Lanes 1-6 correspond to a human genomic DNA (0.3, 0.6, 1.25, 2.5, 5 and 10 ng, respectively), lanes 7-12 to heparin-treated blood (0.3, 0.6, 1.25, 2.5, 5 and 10 µl, respectively), lanes 13-18 to EDTA-treated blood (0.3, 0.6, 1.25, 2.5, 5 and 10 µl, respectively), and lanes 19-24 to sodium citrate-treated blood (0.3, 0.6, 1.25, 2.5, 5 and 10 µl, respectively). The PCR reactions contain Tricine-buffer (pH 8.7), 2.4% (w/v) trehalose and 4 mg/ml BSA.

As shown in FIG. 12, the direct PCR reactions using Tricine-buffer at pH 8.7 accommodated 2.5% (v/v) heparin-treated blood and 5% (v/v) EDTA- or sodium citrate-treated blood. RCR reactions using isolated human DNA (Promega, Inc.) as a template rather showed less specific results in which several bands other than p53 band were observed. Using blood samples per se as a template renders PCR reactions to be under conditions for Hot Start PCR in which a target DNA initially interacts with primers at the first-cycle annealing step because cells in blood are disrupted at much higher temperature.

Where 2.4% trehalose and 4 mg/ml BSA contained in Tricine-buffer (pH 8.7) were used, the direct amplification reactions generated amplicons for up to 5% (v/v) heparin- or sodium citrate-treated blood and 10% (v/v) EDTA-treated blood.

Example IV

Direct PCR for Template DNA with High GC Content

It has been reported that template DNAs with high GC content could be PCR-amplified using betaine, tetramethylammonium chloride (TMAC) or dimethylsulfoxide (DMSO).

To assess whether the direct PCR for templates or primers with high GC content is successful when using such additives, the direct PCR using Tricine-buffer (pH 8.7) and betaine was performed. The amplification reactions for the retinoblastoma (RB) gene used sense primer (E1SD, 5'-CAGGA-CAGCGGCCCGGAG-3') (SEQ ID NO:6) and antisense primer (11SD, 5'-CTGCAGACGCTCCGCCGT-3') (SEQ ID NO:7) to obtain 180 bp amplicon; for the apolipoprotien E (apoE) gene, sense primer (apoE-f, 5'-GGCACGGCTGTC-CAAGGA-3') (SEQ ID NO:8) and antisense primer (apoE-r, 5'-CTCGCGGATGGCGCTGAG-3') (SEQ ID NO:9) to obtain 268 bp amplicon. Since the two primer sets have the high GC content, they generated no amplicons of interest in general PCR process.

The direct PCR reactions were carried out using 50 μl total volume of reaction mixtures containing 5 μl of 10× concentrated PCR buffer, 0.2 mM dNTPs mixture, 0.4 μM primers, 2.0 unit AmpliTaq DNA polymerase (Applied Biosystems, Inc.) and 1 μl of heparin-treated blood samples. The PCR reactions were conducted under the following thermal conditions: 10 min at 94° C. followed by 40 cycles of 30 sec at 94° C., 30 sec at 60° C., and 1 min at 72° C.; followed by a 7 min final extension at 72° C. Tris-buffer (pH 8.3) was used for human genome DNA template (Promega, Inc.) and Tricine-buffer (pH 8.7) containing trehalose for heparin-treated blood template. The concentrations of betaine used were adjusted to 0, 0.5, 1.0, 1.5, 2.0 and 2.5 M.

Figure 14:
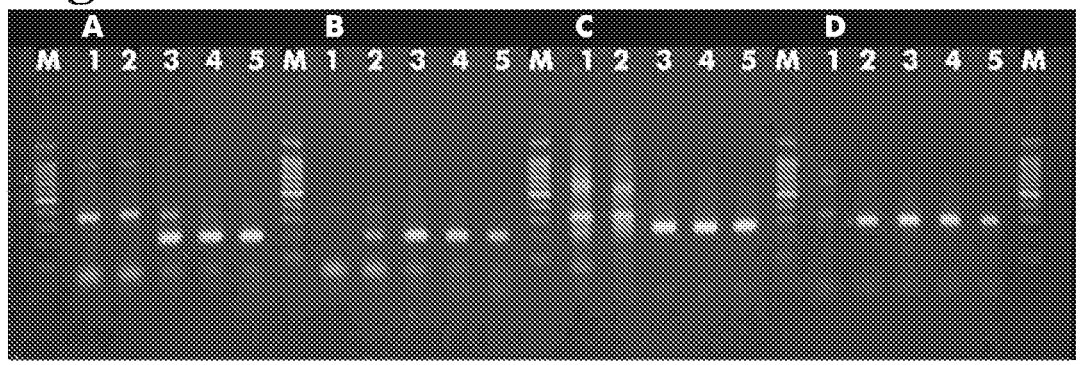
FIG. 14 shows the direct PCR results for amplifying the human retinoblastoma gene (panels A and B, 180 bp) or the apolipoprotein E gene (panels C and D, 268 bp) using betaine under conditions provided by this invention. 20 ng of a human genomic DNA (panels A and C) or 1 µl of heparin-treated blood (panels B and D) was used as templates. The final concentrations of betaine in lanes 1-5 are 0, 0.5, 1.0, 1.5, 2.0 and 2.5 M, respectively.

As shown in FIG. 14, the direct PCR using the Good buffer and above 1.0 M betaine produced amplicons of interest. Accordingly, it would be appreciated that the direct amplification for amplifying templates with high GC content can be successfully conducted in the presence of additives (e.g., betaine, TMAC and DMSO) for overcoming problems derived from templates with high GC content when using a Good buffer and/or non-reducing carbohydrate.

Example V

Amplification for Low-Copy Templates Using Chemically Modified Taq Polymerase Nishimura et al. have suggested that the direct PCR for blood samples could be accomplished using Tris, CHES or CAPSO at above pH 9.0. However, if pH of PCR reaction mixtures is higher, chemical-modified polymerases for Hot Start PCR such as AmpliTaq Gold DNA polymerase (Applied Biosystems, Inc.), FastStart Taq DNA polymerase (Roche Applied Science, Inc.) and HotStarTaq DNA polymerase (Qiagen, Inc.) show no or less regeneration.

Since Good buffers and/or non-reducing carbohydrates can block the action of inhibitors present in biological specimens even at low pH (e.g., 8.3) as demonstrated hereinabove, the Hot Start PCR using such chemical-modified polymerases is successfully performed under conditions of the present invention.

Amplification reactions for infectious diseases or forensic science usually use nucleic acid samples with low copy number. In particular, for diagnosis of infectious diseases such as HIV- and HBV-associated diseases, earlier detection of viral infection is very important. In other words, viral nucleic acid molecules present in low copy number have to be amplified for giving accurate and reliable diagnosis results. According to the present invention, HIV-1 in low copy number can be amplified using chemical-modified Taq polymerase under conditions in which a Good buffer and non-reducing carbohydrates are employed.

Al-Soud et al.(37) have amplified DNA molecules from *Listria monocytogenes* in blood samples using AmpliTaq Gold DNA polymerase and high-concentrated BSA. However, they have not provided amplification results on low copy DNA molecules. Although Kato et al. (U.S. Pat. No. 6,413,747) have suggested amplification results using polyamines on low copy DNA molecules, they have not employed blood samples directly. Instead, they indirectly used collected leukocyte samples having added HIV DNA molecules, which was free from PCR inhibitors including hemoglobin and immunoglobulin G molecules.

PCR reactions for HIV-1(26, 31, 38) in low copy number were carried out using 50 μl total volume of reaction mixtures containing Tricine-buffer (pH 8.3), 0.2 mM dNTPs mixture, 0.5 μM primers, 2.5 mM $MgCl_2$, 2.5 unit AmpliTaq Gold DNA polymerase or HotStarTaq DNA polymerase and 1 μl of heparin-treated blood sample. 2.4% trehalose and 4 mg/ml BSA were used as additives. The nucleotide sequences of primer sets used are:

```
TABLE-US-00001
                                         (SEQ ID NO: 10)
SK145    (5'-AGTGGGGGACATCAAGCAGCCATGCAAAT-3')
and (SEQ ID NO: 11)
SK431    (5'-TGCTATGTCAGTTCCCCTTGGTTCTCT-3');
or (SEQ ID NO: 12)
SK38     (5'-ATAATCCACCTATCCCAGTAGGAGAAAT-3')
and (SEQ ID NO: 13)
SK39     (5'-TTTGGTCCTTGTCTTATGTCCAGAATGC-3').
```

The copy number of HIV-1 DNA (HIV-1 positive control DNA, Applied Biosystems, Inc.) was increased by 10 from 0 to 50. To examine amplification for low-copy DNA with varying blood content, 20 copies of HIV-1 DNA were added to 0, 1, 2, 3, 4, 5 and 6 μl of heparin-treated blood, respectively.

The PCR reactions for SK145 and SK431 primer set were conducted under the following thermal conditions: 15 min at 95° C. followed by 45 cycles of 30 sec at 94° C. and 1 min at 60° C.; followed by a 10 min final extension at 60° C. The amplicons were 142 bp in size. For SK38 and SK39 primer set, the amplifications were carried out under the following thermal conditions to yield 115 bp amplicons: 15 min at 95° C. followed by 45 cycles of 30 sec at 94° C., 1 min at 55° C. and 1 min at 72° C.; followed by a 7 min final extension at 72° C.

Figure 15:
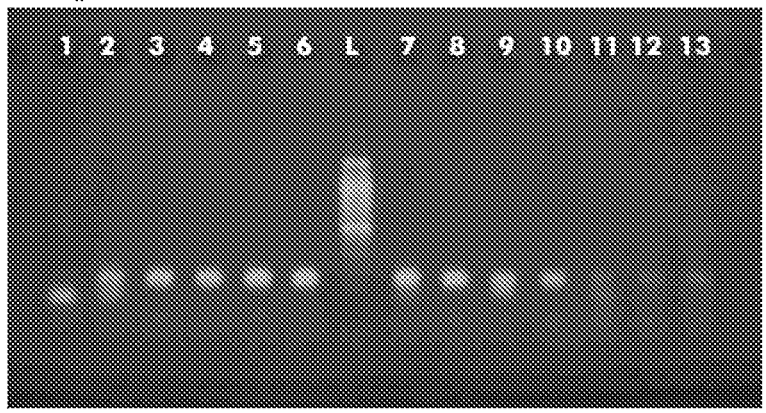
FIG. 15 shows the direct PCR results for amplifying a nucleotide sequence of HIV-1 (human immunodeficiency virus-1) with varying copy number and amount of blood samples. The PCR reactions contain Tricine-buffer (pH 8.3), 2.8% (w/v) trehalose and 4 mg/ml BSA. Lanes 1-6 correspond to 1 µl heparin-treated blood containing 0, 10, 20, 30, 40 and 50 copies of HIV-1 plasmid, respectively, and lanes 7-13 to 20 copies of HIV-1 plasmid contained in 0, 1, 2, 3, 4, 5 and 6 µl heparin-treated blood samples, respectively. The primer set, SK145 and SK431, was used to generate 142 bp amplicon.
Figure 16:
FIG. 16 shows the direct PCR results for amplifying a nucleotide sequence of HIV-1 (human immunodeficiency virus-1) with varying copy number and amount of blood samples. The PCR reactions contain Tricine-buffer (pH 8.3), 2.8% (w/v) trehalose and 4 mg/ml BSA. Lanes 1-6 correspond to 1 µl heparin-treated blood containing 0, 10, 20, 30, 40 and 50 copies of HIV-1 plasmid, respectively, and lanes 7-13 to 20 copies of HIV-1 plasmid contained in 0, 1, 2, 3, 4, 5 and 6 µl heparin-treated blood samples, respectively. The primer set, SK38 and SK39, was used to generate 115 bp amplicon.

As represented in FIG. 15 using AmpliTaq Gold DNA polymerase, 10 copies present in 6 μl of heparin-treated blood and 20 copies present in up to 6% (v/v) blood could be evidently detected by PCR in accordance with the present invention. Twenty copies present in 8-12% (v/v) blood also generated amplicons. Amplifications using HotStarTaq DNA polymerase represented similar results to those of AmpliTaq Gold DNA polymerase, as shown in FIG. 16.

Accordingly, it could be recognized that the present invention using a Good buffer and/or non-reducing carbohydrate enables chemical-modified DNA polymerase for Hot Start PCR to work by regeneration, permitting the direct detection of low copy nucleic acid molecules present in biological specimens such as blood.

Example VI

Test on Other Thermostable DNA Polymerases

Thermostable DNA polymerases developed so far include Pfu DNA polymerase (Stratagene, Inc.) and Pwo DNA polymerase having high fidelity (Roche Applied Science, Inc.), and Tth DNA polymerase having reverse transcription activity (Roche Applied Science, Inc.) as well as Taq DNA polymerase. We examined whether the direct amplification using various thermostable DNA polymerases could be conducted under conditions provided by the present invention. For comparison, we also used commercially available reaction mixtures [20 mM Tris (pH 8.8), 10 mM KCl, 10 mM $(NH_4)_2SO_4$, 0.1% Triton X-100, 100 μg/ml BSA and 2 mM $MgSO_4$ for Pfu DNA polymerase; 10 mM Tris (pH 8.85), 25 mM KCl, 5 mM $(NH_4)_2SO_4$ and 2 mM $MgSO_4$ for Pwo DNA polymerase; and 10 mM Tris (pH 8.9), 100 mM KCl, 50 μg/ml BSA, 0.05% (w/v) Tween 20 and 1.5 mM $MgCl_2$ for Tth DNA polymerase]. The direct PCR for amplifying the p53 gene were carried out using 2.0 unit of each polymerase. The primers used are: forward primer, E8f (5'-GACAAGGGTGGTTGG-GAGTAGATG-3') (SEQ ID NO:14) and reverse primer, E-R2 (5'-CACAAACACGCACCTCAAAG-3') (SEQ ID NO:15). The size of amplicons produced is 357 bp. The PCR thermal cycling conditions are the same as described in Example I.

Figure 17:
FIG. 17 shows the amplification results of the p53 gene using various thermostable DNA polymerases. Lanes 1-5 correspond to Pfu DNA polymerase, lanes 6-10 to Pwo DNA polymerase and lanes 11-15 to Tth DNA polymerase. Lanes 1, 6 and 11 correspond to Tris-buffer (pH 8.3), lanes 2, 7 and 12 to Tris-buffer (pH 8.7), lanes 3, 8 and 13 to Tricine-buffer (pH 8.3) and lanes 4, 9 and 14 to Tricine-buffer (pH 8.7), all of which contain 2.4% trehalose. Each of lanes 5, 10 and 15 uses the reaction mixture provided by commercial manufacturers.

As shown in FIG. 17, while the conventional reaction mixtures gave no amplicons (lanes 5, 10 and 15), the reaction mixtures of this invention (pH 8.3 and 8.7) gave detectable amplicons on agarose gel.

Example VII

Cell Culture-Derived Amplification Inhibition

Animal cell culture is a general process frequently conducted in molecular biology. PCR inhibitors present in cell culture are great obstacles to the direct amplification using cultured cells. According to the amplification developed so far, culture cells are harvested by centrifugation and then subjected to DNA purification followed by PCR process.

To verify whether the present amplification system can overcome obstacles associated with cell culture, the direct PCR for amplifying the p53 gene was carried out using reaction mixtures containing Tricine-buffer (pH 8.7), 2.4% trehalose, cell culture media and 10 ng human genome DNA (Promega, Inc.) as a template. The cell culture medium used is DMEM (Dulbecco's modified Eagle's medium) supplemented with 10% fetal bovine serum (FBS), 100 μg/ml penicillin and 100 μg/ml streptomycin. The primers and conditions for PCR reactions are the same as described in Example I.

Figure 18:
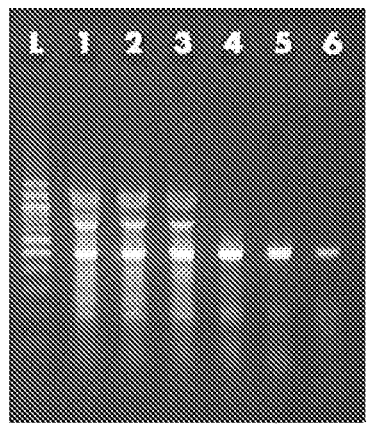
FIG. 18 shows the PCR results for amplifying the p53 gene in cell culture media. Tricine-buffer (pH 8.7) containing 2.4% trehalose was used. As templates, 10 ng of a human genome DNA were used. Lanes 1-6 represent 2, 5, 10, 15 and 20 µl of cell culture media (DMEM containing 10% FBS), respectively.

The results address that the present invention completely overcome inhibition to cell culture-derived amplification (FIG. 18).

Example VIII

Amplification Using Oral Epithelial Cells

Oral epithelial cells were collected using a brush, dried and suspended in 500 μl TE (10 mM Tris and 0.1 mM EDTA, pH 8.0). 2.5 μl of the cell suspension was used for amplification using the AmpFLSTR® Identifiler® kit (Applied Biosystems, Inc.) in accordance with manufacturer's instructions. The reaction mixture (25 μl) was newly prepared to comprise Tricine-buffer (pH 8.3) containing 2.4% trehalose and 4 mg/ml BSA, 0.2 mM dNTP, 2.5 unit AmpliTaq Gold DNA polymerase and AmpFLSTR Identifer primer set. The amplified products by the AmpFLSTR® Identifiler® kit were analyzed using ABI Prism Genotyper 3.7 (Applied Biosystems, Inc.).

Figure 19:
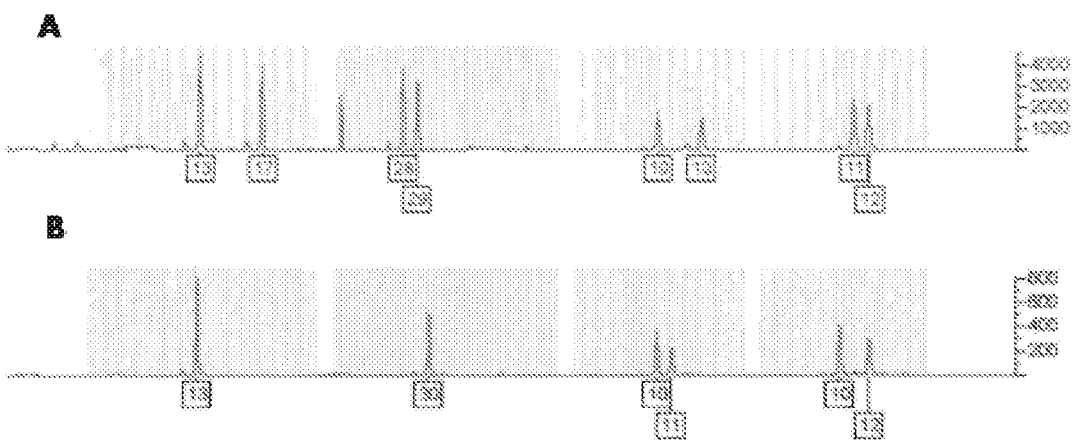
FIG. 19 shows the Blue dye results among analysis results obtained by the AmpFLSTR® Identifiler® kit (Applied Biosystems, Inc.) using saliva (panel A) or blood (panel B). The reaction mixtures used contain trehalose as agents for preventing biological specimens from inhibiting amplification reactions.

The Panel A of FIG. 19 shows the Blue dye result among analysis results obtained from ABI Prism Genotyper 3.7 for DNA molecules in oral epithelial cells amplified by the AmpFLSTR® Identifiler® kit, demonstrating that the present invention using a Good buffer and/or non-reducing carbohydrate can block the action of PCR inhibitors contained in cell suspensions to permit a successful DNA fingerprinting using cells rather than purified DNA samples. In addition, it is noteworthy that the reaction mixture prepared according to the present invention enables AmpliTaq Gold DNA polymerase to be active in the amplification reactions using cell suspension.

Example IX

Gene Testing in Forensic Science

In forensic science, a gene test becomes highlighted and its related technologies are rapidly developed. However, the gene test in forensic science generally encounters the problems associated with samples to be analyzed such as various types and states of samples. In order words, gene amplification reactions are to be performed using various samples such as clear, decomposed or contaminated samples, or trace amount of sample. In addition to this, the gene test in forensic science usually requires prompt results.

We examined whether the present invention can satisfy the requirements for the gene testing in forensic science. 2.5 μl of blood diluted by 40-50 fold with TE buffer was used as samples and the AmpFLSTR® Identifiler® kit (Applied Biosystems, Inc.) was used for DNA fingerprinting. The amplification reaction and analysis were performed as described in Example VIII.

As shown in the Panel B of FIG. 19, the present invention using a Good buffer and/or non-reducing carbohydrate can block the action of PCR inhibitors contained in blood to permit a successful DNA fingerprinting using blood rather than purified DNA samples. In addition, it is noteworthy that the reaction mixture prepared according to the present invention enables AmpliTaq Gold DNA polymerase to be active in the amplification reactions using blood samples.

Example X

Synthesis of cDNA from Cultured Cells

Cultured cells (hepG2-SK, 5×10$^6$ cells) were diluted to 1×10$^{3-4}$ cells/μl with phosphate buffered saline (PBS). 1 μl of the diluted cells were added directly to 50 μl of a reaction solution to perform an RT-PCR using a primer specific to a human β-actin mRNA. Alternatively, for performing conventional RT-PCR using isolated RNA, total RNA was purified from hepG2-SK cells by RNeasy Mini Kit (Qiagen, Inc.) and cDNA was subsequently synthesized from 1 μg of the purified RNA by cDNA synthesis kit with oligo(dT)$_{18}$ To distinguish an RNA-derived product from a DNA-derived product in the RT-PCR, primers were designed so that DNA-derived product (370 bp) was 107 bp longer than RNA-derived product (264 bp) by intron-spanning. The sequences of primers used are: b-actin-f (5'-CAA GAG ATG GCC ACG GCT GCT-3') (SEQ ID NO:16) and b-actin-r (5'-TCC TTC TGC ATC CTG TCG GCA-3') (SEQ ID NO:17). The RT-PCR was performed by adding a PCR reaction reagent to an RT reaction product.

The RT reactions were carried out using 25 μl of total volumes of RT reaction mixtures containing 50 mM Tricine (pH 8.7), 80 mM KCl, 2.5 mM MgCl$_2$, 250 μM dNTPs mixture, 5 mM DTT, 0.4 μM b-actin-r primer, 20 units of RNase inhibitor (Promega, Inc.) and 4.5 units of AMV reverse transcriptase (Roche Applied Science, Inc.). RNase-free water was added to reaction as a RT-negative control. The RT reaction was performed at 60° C. for 60 min, followed by 95° C. for 10 min for inactivating the reverse transcriptase.

Figure 20:
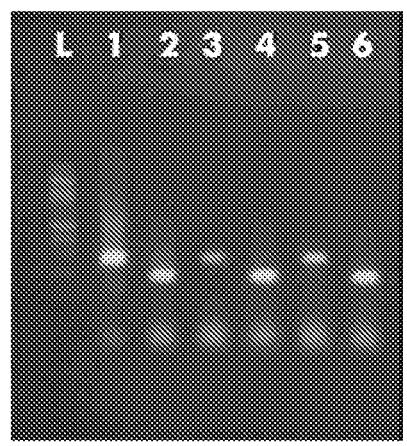
FIG. 20 shows the results of RT-PCR (reverse transcription-polymerase chain reaction) for amplifying the β-actin gene (264 bp) directly using hepG2-SK cells. Lanes 1 and 2 represent the RT-PCR results from human genomic DNA and total cDNA, respectively. Lanes 3-4 correspond to the RT-PCR results directly using $1\times10^3$ cells, and lanes 5-6 to those directly using $1\times10^4$ cells. Lanes 3 and 5 are the results not using reverse transcriptase (RT-negative); lanes 4 and 6 using reverse transcriptase (RT-positive).

After the RT, 10 μmol of the b-actin-f primer and 2 units of Taq DNA polymerase were added to perform the subsequent PCR reaction. In PCR reaction, 10 ng of human genomic DNA (Promega, Inc.) and cDNA synthesized from hepG2-SK were used as PCR control. The PCR reactions were conducted under the following thermal conditions: 2 min at 94° C. followed by 45 cycles of 30 sec at 94° C., 30 sec at 65° C., and 30 sec at 72° C.; followed by a 5 min final extension at 72° C. Amplified products were analyzed by electrophoresis on a 2% agarose gel containing 0.5 μg/ml ethidium bromide and subsequent UV radiation As shown in FIG. 20, an amplification product specific to the human β-actin mRNA was obtained in the RT-PCR performed in the presence of the reverse transcriptase by adding cultured cells directly to the reaction solution.

Example XI

RELP Analysis of Meat 1 mg or 10 mg of bovine meat samples was incubated for 2 hr at 56° C. in 20 mM Tricine buffer (pH 8.0) containing 0.2 mg proteinase K (Sigma-Aldrich, Inc.), 0.3% SDS, 0.6% Tween 20, 5 mM EDTA and 400 mM NaCl and successively for 45 min at 85° C. to obtain a lysate of bovine tissue. The lysate was subjected directly to PCR for amplifying the bovine MC1-R gene and to digestion by 1 U of MspA1I for 45 min at 37° C. to analyze RELP (restriction fragment length polymorphism). The PCR reactions were carried out using 25 μl total volume of PCR reaction mixtures containing 200 μM dNTPs mixture, 0.2 μM primers and 1.25 units AmpliTaq DNA polymerase and 10 mM Tricine (pH 8.3), 50 mM KCl, 2.5 mM $MgCl_2$ and 2.4% (w/v) trehalose. The sequences of primers used are: MC1R-f (5'-CAAGAACCGCAACCTG-CACT-3') (SEQ ID NO:18) and MC1R-r (5'-TGATGAA-GAGCAGGCTGGTG-3') (SEQ ID NO:19). The PCR reactions were conducted under the following thermal conditions: 5 min at 94° C. followed by 40 cycles of 30 sec at 94° C., 30 sec at 62° C., and 1 min at 72° C.; followed by a 10 min final extension at 72° C.

Figure 21:
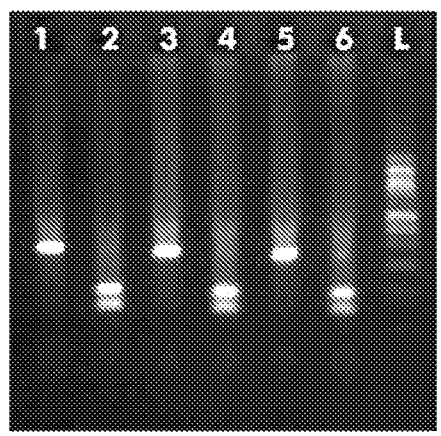
FIG. 21 represents the results of the direct PCR & RFLP (restriction fragment length polymorphism) analysis using lysate samples from bovine meat tissues. Lanes 1-2 correspond to isolated DNA, lanes 3-4 to 1 mg meat lysate, and lanes 5-6 to 10 mg meat lysate template. Lanes 2, 4 and 6 represent the results of MspA1I treatment to amplicons.

As shown in FIG. 21, the direct amplification directly using bovine tissue lysates evidently generated amplicons under conditions provided by the present invention and RFLP analysis results also were obtained.

Example XII

Detection of Food Poisoning-Causing Microbes in Feces

We assessed whether the present invention can overcome the inhibition to PCR by feces samples. *Shigella flexneri* as a representative of food poisoning-causing microbes was incubated for 24 hr at 37° C. on a blood agar plate. One colony generated was suspended in 0.2 ml PBS and its colony forming unit (CFU) was then determined. A feces sample from healthy adult was diluted by 10 fold (v/w) with PBS, vortexed and kept to stand overnight at 4° C. to obtain supernatant. 1 μl of the supernatant and 7 μl of the suspension containing *Shigella flexneri* with determined CFU were mixed to provide a template for PCR amplification. The PCR reactions for amplifying the virA gene of *Shigella flexneri* were carried out using 20 μl total volume of PCR reaction mixtures containing 200 μM dNTPs mixture, each 0.2 μM of primers, vir-f (sense primer, 5'-CTGCATTCTGGCAATCTCTTCACATC-3') (SEQ ID NO:20) and vir-r (antisense primer, 5'-TGAT-GAGCTAACTTCGTAAGCCCTCC-3') (SEQ ID NO:21), 1 unit AmpliTaq DNA polymerase and Tricine-buffer (pH 8.3) containing 2.4% trehalose. 8 μl of the feces suspensions amounting to 5% relative to the total reaction volume, which contained 128,000 CFU, 6,400 CFU, 320 CFU, 16 CFU, 8 CFU, 4 CFU, 2 CFU and 1 CFU, respectively, were used. The PCR reactions were conducted under the following thermal conditions: 5 min at 95° C. followed by 40 cycles of 40 sec at 95° C., 40 sec at 55° C., and 40 sec at 72° C.; followed by a 10 min final extension at 72° C.

We also evaluated whether the present invention could be used for accurate real-time PCR (qPCR) assay to detect and quantify the relative pathogen detection in human feces samples. A feces sample from healthy adult was diluted by 10 fold (v/w) with PBS, vortexed and kept to stand overnight at 4° C. to obtain supernatant. 1 μl of the supernatant and 7 μl of the suspension containing *Shigella flexneri* with known copies were mixed to provide a template to generate standard curve. In other words, 8 μl of the feces suspensions amounting to boiled 5% relative to the total reaction volume, which contained 128,000 CFU, 6,400 CFU, 320 CFU, 16 CFU, 4 CFU and 2 CFU, respectively, were used.

A real-time hot-start PCR was performed with the following reaction mixture on an Mx3000P® QPCR System (Stratagene, Inc.). The 20 μl reaction mixture contained 200 μM dNTPs mixture, each 0.2 μM vir-f and vir-r primers, 1 unit HotStarTaq DNA polymerase (Qiagen, Inc.), Tricine-buffer (pH 8.3) containing 2.4% trehalose, 1×SYBR Green I (Molecular Probes, Inc.) and 0.4×ROX standard for normalization. Thermal profile is: 15 min at 95° C. followed by 50 cycles of 30 sec at 94° C., 30 sec at 60° C., and 30 sec at 72° C. (data acquisition).

Figure 22A:
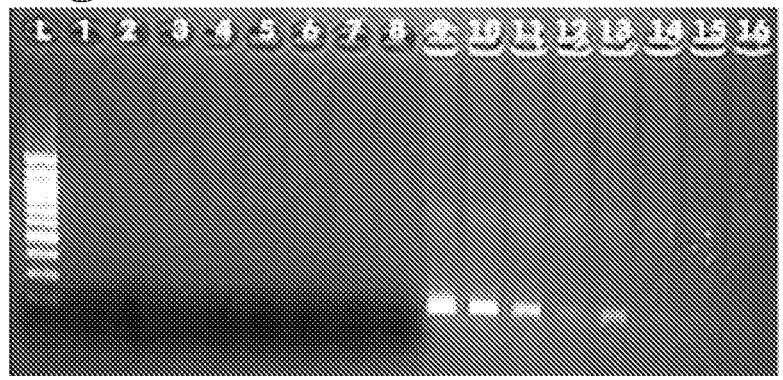
FIG. 22A shows the direct PCR results for amplifying the virA gene directly using feces samples carrying *Shigella flexneri*. Lanes 1-8 represent Tris-buffer (pH 8.3) and lanes 9-16 represent 2.4% (w/v) trehalosre-containing Tricine-buffer (pH 8.3). The titers of *Shigella flexneri* were adjusted to 128,000 CFU (lanes 1 and 9), 6,400 CFU (lanes 2 and 10), 320 CFU (lanes 3 and 11), 16 CFU (lanes 4 and 12), 8 CFU (lanes 5 and 13), 4 CFU (lanes 6 and 14), 2 CFU (lanes 7 and 15), and 1 CFU (lanes 8 and 16).
Figure 22B:
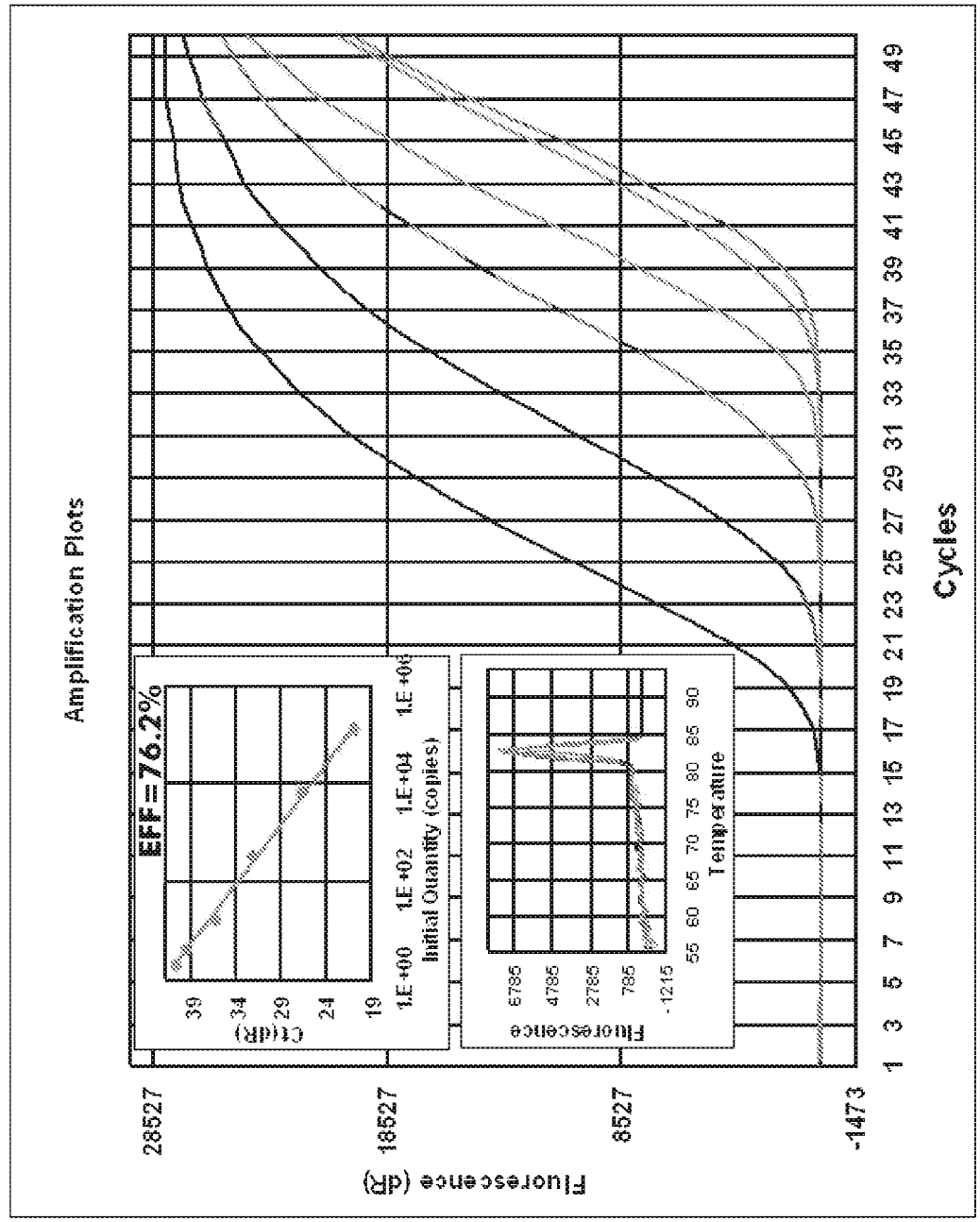
FIG. 22B shows the results of real time PCR. The upper inset shows a standard curve and the lower inset shows a melting curve analysis from SYBR Green I assay representing the virA gene detection of *Shigella flexneri* spiked in feces.

As shown in FIG. 22A, the direct PCR generated amplified products from feces samples having even 8 CFU pathogens under conditions provided by the present invention, while Tris buffer generated no amplicons from feces samples having 128,000 CFU pathogens. These results lead us to reason that Good buffers and/or non-reducing carbohydrates ensure to overcome PCR inhibition derived from feces samples. As shown in FIG. 22B, the PCR products were directly obtained from feces samples having even 2 CFU pathogen under conditions provided by the present invention and analyzed pursuant to the real-time SYBR GREEN quantitative PCR Assay in a rapid manner without any downstream modification of the protocol provided by the manufacturer.

Example XIII

Gene Amplification Using Plant Tissues

Figure 23:
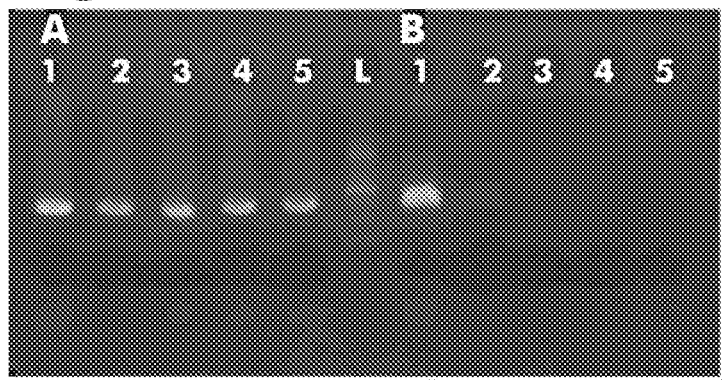
FIG. 23 shows the direct PCR results for amplifying the rice β-actin gene using various plant samples including 20 ng isolated DNA (lane 1), 0.04 mg (lane 2) and 0.1 mg (lane 3) of freeze-dried powder, each 1 μl of 0.04 mg/μl leaf suspension (lane 4) and 0.1 mg/μl leaf suspension (lane 5) from rice leaves. Panel A represents 2.4% trehalose-containing Tricine-buffer (pH 8.3), and panel B represents Tris-buffer (pH 8.3).

Leaves freeze-dried from *Oryza sativa* were grounded to powder samples. 4-10 mg of powder samples was suspended in 100 μl of a suspension buffer (20 mM Tricine buffer, pH 8.0, containing 0.3% SDS, 0.6% Tween 20, 5 mM EDTA and 400 mM NaCl) to obtain a leaf suspension from *Oryza sativa*. 0.04-1 mg of powder or 1 μl of sample suspension was subjected directly to PCR for amplifying the fl-actin gene. The PCR reactions were carried out using 25 μl total volume of PCR reaction mixtures containing 200 μM dNTPs mixture, 0.2 μM primers and 1.25 unit AmpliTaq DNA polymerase. The buffer system was Tricine-buffer (pH 8.3) containing 2.4% (w/v) trehalose (FIG. 23, panel A). For comparison, Tris-buffer (pH 8.3) was also used (FIG. 23, panel B). The nucleotide sequences of primers used are: sense primer, 5'-TCCATCTTGGCATCTCTCAG-3' (SEQ ID NO:22) and antisense primer, 5'-GTACCCGCATCAGGCATCTG-3' (SEQ ID NO:23). The PCR reactions were conducted under the following thermal conditions: 5 min at 94° C. followed by 40 cycles of 30 sec at 94° C., 30 sec at 62° C., and 1 min at 72° C.; followed by a 10 min final extension at 72° C.

In the case that Tricine-buffer (pH 8.3) containing 2.4% (w/v) trehalose was used, all reactions using any template (purified DNA, leaf powder and leaf suspension) produced amplicons (FIG. 23, panel A). In contrast, Tris-buffer generated amplicons only when purified DNA was used as templates (FIG. 23, panel B).

Therefore, it could be appreciated that zwitterionic buffers and/or non-reducing carbohydrates also permit the direct amplification using plant tissues.

Example XIV

Gene Amplification in Tissue Slides

In lung tissues, inter alia, lung cancer tissues, the researches focusing on mutations on exons 18, 19, 20 and 21 of the epidermal growth factor receptor (EGFR) gene have been intensively made for the susceptibility of lung cancer drugs such as gefitinib (Iressa) and elrotilib (tarceva) (39). To verify the possibility of the direct PCR using slide tissues, a spot was extracted from the tissue microarray (ISU Abxis, Inc.) and subjected directly to PCR. Four sets of primers used are: E18F1, 5'-AATGAGCTGGCAAGTGCCGTGTCCTG-3' (SEQ ID NO:24) and E18R1, 5'-CCTCTCAATAACT-TGGGAAAAACACTG-3' (SEQ ID NO:25) for amplifying exon 18 to obtain 425 bp amplicon; E19F1, 5'-AGC-CCCCAGCAATATCAGCCTTAGGTG-3' (SEQ ID NO:26) and E19R1, 5'-ATGGGAGAGGCCAGTGCT-GTCTCTAAG-3' (SEQ ID NO:27) for amplifying exon 19 to obtain 446 bp amplicon; E20F1, 5'-GCATTCATGCGTCT-TCACCTGGAAGG-3' (SEQ ID NO:28) and E2OR1, 5'-GCACACACATATCCCCATGGCAAACTC-3' (SEQ ID NO:29) for amplifying exon 20 to obtain 385 bp amplicon; and E21 F1, 5'-CGCCAGCCATAAGTCCTCGACGTG-GAG-3' (SEQ ID NO:30) and E21R1, 5'-TCTGGAGAG-CATCCTCCCCTGCATGTG-3' (SEQ ID NO:31) for amplifying exon 21 to obtain 386 bp amplicon.

10 µl of 30% glycerol was added dropwise to a tissue spot in the tissue microarray and following 1-2 min, the tissue spot was lyzed by continuous pipetting. 1 µl of the lyzed tissue spot was subjected directly to PCR for amplification. The PCR reactions were carried out using 25 µl total volume of PCR reaction mixtures containing 200 µM dNTPs mixture, 0.3 µM primers and 1.25 unit AmpliTaq DNA polymerase. The buffer system was Tricine-buffer (pH 8.3) containing 2.4% (w/v) trehalose. The PCR reactions were conducted under the following thermal conditions: 5 min at 94° C. followed by 40 cycles of 30 sec at 94° C., 30 sec at 62° C., and 1 min at 72° C.; followed by a 10 min final extension at 72° C.

Figure 24:
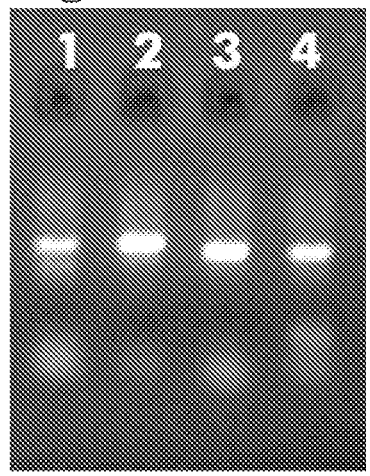
FIG. 24 shows the direct PCR results for amplifying the epidermal growth factor receptor (EGFR) gene directly using a tissue spot extracted from the tissue microarray (ISU Abxis, Inc.). Lanes 1-4 correspond to exon 18. 19. 20 and 21 of the EGFR gene, respectively. Tricine-buffer (pH 8.3) containing 2.4% trehalose was used.

As shown in FIG. 24, the tissue slide can be directly amplified without DNA purification in accordance with the present invention.

Example XV

SNP Genotyping

SNP stands for "single nucleotide polymorphism". SNPs are the most common genetic variations and it occur once every 100 to 300 bases. Many SNP genotyping technologies have been developed in the past few years. Nevertheless, there is a need in the art for fast, reliable and inexpensive SNP genotyping methods.

We examined whether the present invention can be applied to SNP genotyping. For SNP genotyping, the primers were designed so that amplicon (525 bp) contains the −216G/T polymorphism in the promoter region of the EGFR gene. The sequences of primers used are: egfr-f (5'-GGCCCGCGC-GAGCTAGACGT-3') (SEQ ID NO:32) and egfr-r (5'-CAG-GTGGCCTGTCGTCCGGTCT-3') (SEQ ID NO:33).

0.5 µl of blood was subjected directly to 25 µl of total volume of PCR reaction mixtures containing 200 µM dNTPs mixture, 0.3 µM primers and 1.25 unit AmpliTaq DNA polymerase. The buffer system was Tricine-buffer (pH 8.3) containing 2.4% (w/v) trehalose. The PCR reactions were conducted under the following thermal conditions: 5 min at 94° C. followed by 40 cycles of 30 sec at 94° C., 30 sec at 60° C., and 30 sec at 72° C.; followed by a 10 min final extension at 72° C. PCR products were then purified by treatment with ExoSAP-IT (USB, Inc.) or by QIAquick PCR Purification Kit (Qiagen, Inc.). Purified PCR product was then used to perform single base extension to genotype the −216G/T polymorphism with a primer egfr-sbe (5'-GCGCGGCCGCAG-CAGCCTCC-3') (SEQ ID NO:34) and the SNaPshot kit (Applied Biosystems, Inc.) in accordance with manufacturer's instructions and genotype was scored.

Figure 25:
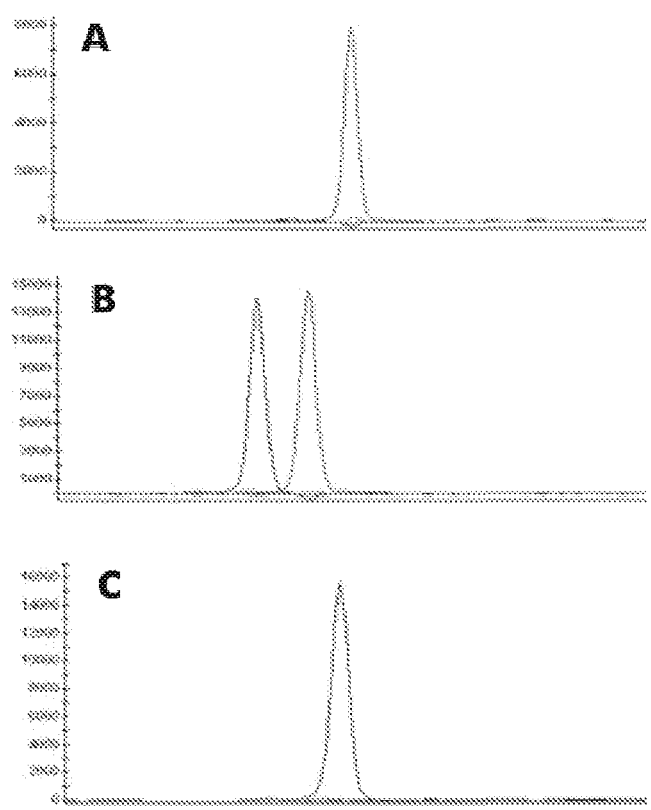
FIG. 25 represents the electropherogram of SNaPshot ddNTP Primer-Extension Assay analyzed on the ABI 3100 Genetic analyzer for SNP (single nucleotide polymorphism) genotyping to detect polymorphisms of the promoter region of the EGFR gene (top graph, TT homozygote; middle graph, GT heterozygote; and bottom graph, GG homozygote).

As shown in FIG. 25, the PCR products were directly obtained from blood under the conditions provided by the present invention and used as templates for ABI PRISM® SNaPshot® ddNTP Prime-Extension Assay without any downstream modification of the protocol provided by the manufacturer, thereby yielding the precise results of SNP genotyping.

Example XVI

Fluorescent Dye-Terminator Cycle Sequencing

DNA sequencing is the determination of the precise nucleotide sequences in a DNA sample. The most predominant method for executing this is called the fluorescent dideoxy method. We examined whether the present invention can be applied to the automated fluorescent dye-terminator cycle sequencing. For automated cycle sequencing, the primers were designed so that amplicon (406 bp) contains HVI segment of D-loop region in human mitochondrial DNA. The sequences of primers used are: L15996 (5'-CTCCACCATT-AGCACCCAAAG-3') (SEQ ID NO:35) and H16401 (5'-TGATTTCACGGAGGATGGTG-3') (SEQ ID NO:36). 1 µl of blood was subjected directly to 25 µl of total volume of PCR reaction mixtures containing 200 µM dNTPs mixture, 0.2 µM primers and 1.25 unit AmpliTaq DNA polymerase (Applied Biosystems, Inc.). The buffer system was Tricine-buffer (pH 8.3) containing 2.4% (w/v) trehalose. The PCR reactions were conducted under the following thermal conditions: 5 min at 94° C. followed by 35 cycles of 45 sec at 94° C., 45 sec at 58° C., and 45 sec at 72° C.; followed by a 5 min final extension at 72° C.

The half of PCR products were then purified by NucleoSpin® Extract II (Macherey-Nagel, Inc.) or by treatment with ExoSAP-IT (USB, Inc.) and the rest were not purified. Purified or unpurified PCR product was then sequenced using BigDye terminator v3.1 cycle sequencing reaction (Applied Biosystems, Inc.) with L15996/H406 primer to extend forward/reverse strands in accordance with manufacturer's instructions.

Figure 26A:
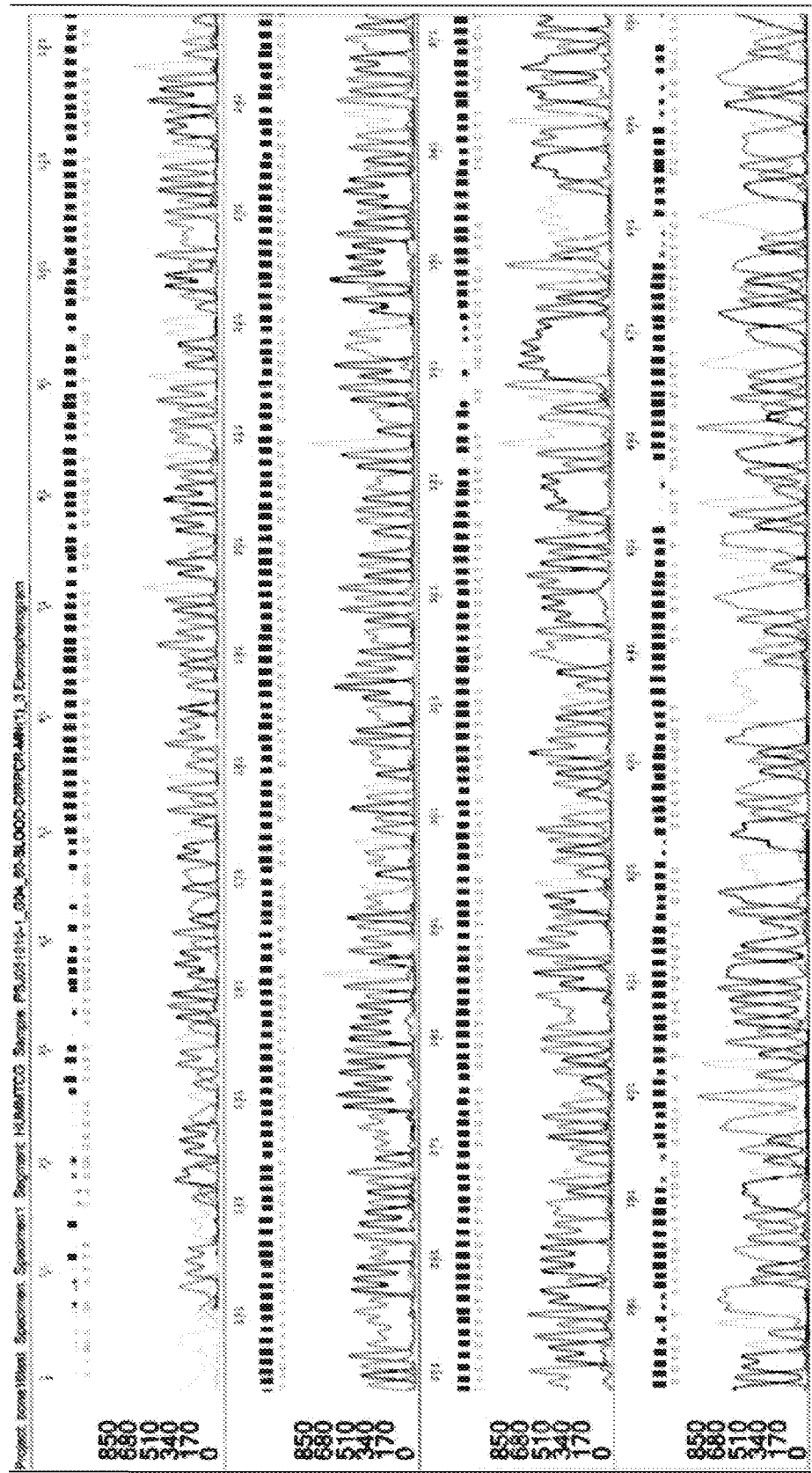
FIGS. 26A and 26B represent the sequencing data from the fluorescent dye-terminator cycle sequencing. Before cycle sequencing, the direct PCR product underwent PCR clean-up with NucleoSpin Extract II (FIG. 26A) or not purified (FIG. 26B).
Figure 26B:
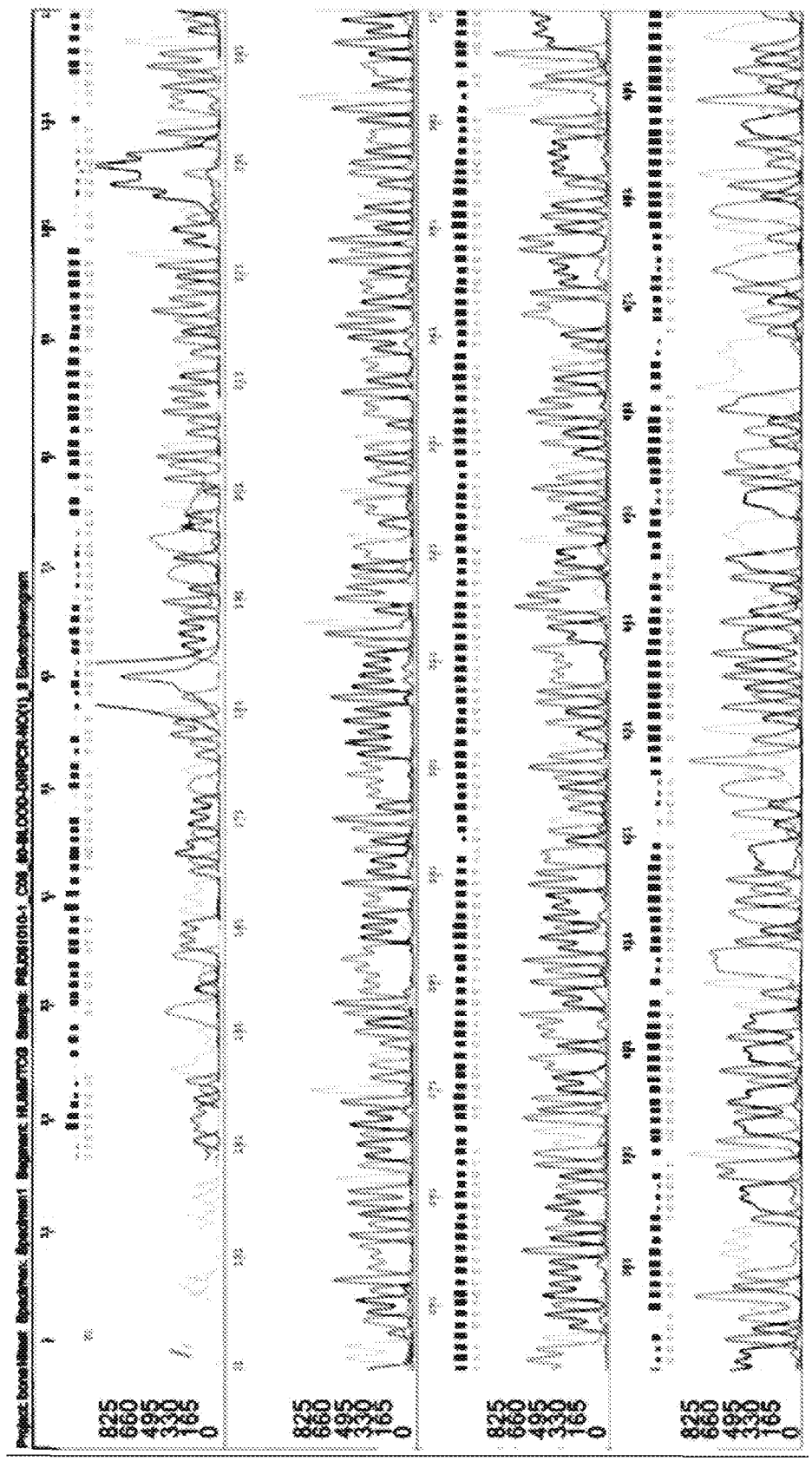

As shown in FIGS. 26A-26B, the PCR products were directly given from blood under the conditions provided by the present invention and used as templates for ABI PRISM® BigDye terminator v3.1 cycle sequencing reaction without any downstream modification of the protocol provided by the manufacturer, finally yielding the results of DNA sequencing.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

1. Saiki, R. K., Scharf, S., Faloona, F., Mullis, K. B., Horn, G. T., Erlich, H. A. & Arnheim, N. (1985) *Science* 230, 1350-1354.
2. Mullis, K. B. & Faloona, F. A. (1987) *Methods Enzymol.* 155, 335-350.
3. Saiki, R. K., Gelfand, D. H., Stoffel, S., Scharf, S. J., Higuchi, R., Horn, G. T., Mullis, K. B. & Erlich, H. A. (1988) *Science* 239, 487-491.
4. Akane, A., Matsubara, K., Nakamura, H., Takahashi, S. & Kimura, K. (1994) *J. Forensic Sci.* 39, 362-372.
5. Al Soud, W. A., Jonsson, L. J. & Radstrom, P. (2000) *J. Clin. Microbiol.* 38, 345-350.
6. Mercier, B., Gaucher, C., Feugeas, O. & Mazurier, C. (1990) *Nucleic Acids Res.* 18, 5908.

7. Panaccio, M. & Lew, A. (1991) *Nucleic Acids Res.* 19, 1151.
8. McCusker, J., Dawson, M. T., Noone, D., Gannon, F. & Smith, T. (1992) *Nucleic Acids Res.* 20, 6747.
9. Panaccio, M., Georgesz, M. & Lew, A. M. (1993) *Biotechniques* 14, 238-243.
10. Sarkar, G., Kapelner, S. & Sommer, S. S. (1990) *Nucleic Acids Res.* 18, 7465.
11. Burckhardt, J. (1994) *PCR Methods Appl.* 3, 239-243.
12. Kreader, C. A. (1996) *Appl. Environ. Microbiol.* 62, 1102-1106.
13. Cheyrou, A., Guyomarc'h, C., Jasserand, P. & Blouin, P. (1991) *Nucleic Acids Res.* 19, 4006.
14. Makowski, G. S., Davis, E. L., Aslanzadeh, J. & Hopfer, S. M. (1995) *Nucleic Acids Res.* 23, 3788-3789.
15. Satoh, Y., Takasaka, N., Hoshikawa, Y., Osaki, M., Ohfuji, S., Ito, H., Kaibara, N., Kurata, T. & Sairenji, T. (1998) *J. Clin. Microbiol.* 36, 3423-3425.
16. Abu Al-Soud, W. & Radstrom, P. (2000) *J. Clin. Microbiol.* 38, 4463-4470.
17. Wu, D. Y. & Wallace, R. B. (1989) *Genomics* 4, 560-569.
18. Barany, F. (1991) *PCR Methods Appl.* 1, 5-16.
19. Kwoh, D. Y., Davis, G. R., Whitfield, K. M., Chappelle, H. L., DiMichele, L. J. & Gingeras, T. R. (1989) *Proc. Natl. Acad. Sci. U.S. A* 86, 1173-1177.
20. Guatelli, J. C., Whitfield, K. M., Kwoh, D. Y., Barringer, K. J., Richman, D. D. & Gingeras, T. R. (1990) *Proc. Natl. Acad. Sci. U.S. A* 87, 1874-1878.
21. Walker, G. T., Little, M. C., Nadeau, J. G. & Shank, D. D. (1992) *Proc. Natl. Acad. Sci. U.S. A* 89, 392-396.
22. Walker, G. T., Fraiser, M. S., Schram, J. L., Little, M. C., Nadeau, J. G. & Malinowski, D. P. (1992) *Nucleic Acids Res.* 20, 1691-1696.
23. Notomi, T., Okayama, H., Masubuchi, H., Yonekawa, T., Watanabe, K., Amino, N. & Hase, T. (2000) *Nucleic Acids Res.* 28, E63.
24. Don, R. H., Cox, P. T., Wainwright, B. J., Baker, K. & Mattick, J. S. (1991) *Nucleic Acids Res.* 19, 4008.
25. D'Aquila, R. T., Bechtel, L. J., Videler, J. A., Eron, J. J., Gorczyca, P. & Kaplan, J. C. (1991) *Nucleic Acids Res.* 19, 3749.
26. Chou, Q., Russell, M., Birch, D. E., Raymond, J. & Bloch, W. (1992) *Nucleic Acids Res.* 20, 1717-1723.
27. Ruano, G., Fenton, W. & Kidd, K. K. (1989) *Nucleic Acids Res.* 17, 5407.
28. Noonan, K. E. & Roninson, I. B. (1988) *Nucleic Acids Res.* 16, 10366.
29. Dang, C. & Jayasena, S. D. (1996) *J. Mol. Biol.* 264, 268-278.
30. Lin, Y. & Jayasena, S. D. (1997) *J. Mol. Biol.* 271, 100-111.
31. Kellogg, D. E., Rybalkin, I., Chen, S., Mukhamedova, N., Vlasik, T., Siebert, P. D. & Chenchik, A. (1994) *Biotechniques* 16, 1134-1137.
32. Birch, D. E. (1996) *Nature* 381, 445-446.
33. Good, N. E., Winget, G. D., Winter, W., Connolly, T. N., Izawa, S. & Singh, R. M. (1966) *Biochemistry* 5, 467-477.
34. Lyamichev, V., Mast, A. L., Hall, J. G., Prudent, J. R., Kaiser, M. W., Takova, T., Kwiatkowski, R. W., Sander, T. J., de Arruda, M., Arco, D. A. et al. (1999) *Nat. Biotechnol.* 17, 292-296.
35. Ryan, D., Nuccie, B. & Arvan, D. (1999) *Mol. Diagn.* 4, 135-144.
36. Ohnishi, Y., Tanaka, T., Ozaki, K., Yamada, R., Suzuki, H. & Nakamura, Y. (2001) *J. Hum. Genet.* 46, 471-477.
37. Abu Al-Soud, W. & Radstrom, P. (1998) *Appl. Environ. Microbiol.* 64, 3748-3753.
38. Christopherson, C., Sninsky, J. & Kwok, S. (1997) *Nucleic Acids Res.* 25, 654-658.
39. Qin, B. M., Chen, X., Zhu, J. D. & Pei, D. Q. (2005) *Cell Res.* 15, 212-217.

What is claimed is:

1. A method for preventing a biological specimen from inhibiting a direct enzymatic reaction involving a nucleic acid molecule, the method comprising:
   (a) adding a non-reducing carbohydrate to a reaction mixture before contacting the biological specimen to the reaction mixture; wherein the non-reducing carbohydrate is a trehalose and its final concentration in the reaction mixture is at 6% (w/v) to 30% (w/v);
   (b) contacting the biological specimen to the reaction mixture further comprising a tricine zwitterioninc buffer having a pH 8.3-8.9, wherein the nucleic acid molecule present in the biological specimen is not purified before the enzymatic reaction; and
   (c) performing the enzymatic reaction directly using the biological specimen in the reaction mixture with preventing the biological specimen from inhibiting the direct enzymatic reaction by the non-reducing carbohydrate.

2. The method according to claim 1, wherein said enzymatic reaction involving a nucleic acid molecule is an amplification reaction, a reverse transcription, a DNA ligation, a nuclease-mediated reaction or a DNA methylation.

3. The method according to claim 2, wherein said enzymatic reaction is the amplification reaction.

4. The method according to claim 3, wherein said amplification reaction is Hot Start PCR (polymerase chain reaction).

5. The method according to claim 3, wherein said amplification reaction is RT-PCR (reverse transcription-polymerase chain reaction).

6. The method according to claim 2, wherein said enzymatic reaction is the nuclease-mediated reaction.

7. The method according to claim 6, wherein said the nuclease-mediated reaction is Invader assay.

8. The method according to claim 1, wherein said biological specimen is virus, lymph, myeloid fluid, saliva, milk, urine, feces, ocular fluid, semen, brain extracts, spinal cord fluid, joint fluid, thymic fluid, ascitic fluid, or amniotic fluid.

9. The method according to claim 1, wherein said reaction mixture further comprises a zwitterionic surfactant, a bovine serum albumin, a polyamine or their combination.

10. The method according to claim 1, wherein said biological specimen is blood.

11. The method according to claim 10, wherein said biological specimen is blood and the nucleic acid molecule present in blood has a low copy number.

12. The method according to claim 1, wherein said biological specimen is bacteria, tissue, cell, or cell tissue fluid.

* * * * *